US012711614B2

(12) United States Patent
Endo

(10) Patent No.: US 12,711,614 B2
(45) Date of Patent: Aug. 18, 2026

(54) MEDICAL IMAGE PROCESSING SYSTEM FOR DETECTING FAILURE AND METHOD FOR OPERATING THE SAME

(71) Applicant: FUJIFILM Corporation, Tokyo (JP)

(72) Inventor: Hisashi Endo, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 711 days.

(21) Appl. No.: 18/185,930

(22) Filed: Mar. 17, 2023

(65) Prior Publication Data

US 2023/0301500 A1 Sep. 28, 2023

(30) Foreign Application Priority Data

Mar. 24, 2022 (JP) ................................ 2022-048170

(51) Int. Cl.
*G06T 7/00* (2017.01)
*A61B 1/00* (2006.01)
*G06V 20/40* (2022.01)

(52) U.S. Cl.
CPC .......... *G06T 7/0012* (2013.01); *A61B 1/0002* (2013.01); *G06V 20/40* (2022.01)

(58) Field of Classification Search
None
See application file for complete search history.

(56) References Cited

U.S. PATENT DOCUMENTS 5,373,327 A 12/1994 McGee et al.
2003/0033062 A1 2/2003 Nishina
2006/0116586 A1* 6/2006 Sekiguchi ................ A61B 1/12 600/470
2013/0012777 A1* 1/2013 Baum ................ A61B 1/00165 600/110
2013/0083179 A1* 4/2013 Kotani ............... A61B 1/00009 348/E7.085
2015/0065803 A1* 3/2015 Douglas .................. G06T 7/143 600/200

(Continued)

FOREIGN PATENT DOCUMENTS

JP H05-5633 A 1/1993
JP H07-075128 A 3/1995

(Continued)

OTHER PUBLICATIONS

An Office Action; "Notice of Reasons for Refusal," mailed by the Japanese Patent Office on Sep. 2, 2025, which corresponds to Japanese Patent Application No. 2022-048170 and is related to U.S. Appl. No. 18/185,930; with English language translation.

*Primary Examiner* — Frank Johnson
(74) *Attorney, Agent, or Firm* — Studebaker Brackett PLLC

(57) ABSTRACT

A medical image processing system includes an external device having a processor, and an endoscope system, in which the processor is configured to acquire a real-time medical video image from the endoscope system during endoscopy, receive a trigger signal having information regarding failure occurrence created based on a failure scene of the medical video image from the endoscope system, temporarily store the medical video image, extract a failure video image having the failure scene from the temporarily stored medical video image based on a reception timing of the trigger signal, and store the failure video image in a main storage region.

15 Claims, 18 Drawing Sheets

(56) References Cited

U.S. PATENT DOCUMENTS

| | | | | |
|---|---|---|---|---|
| 2017/0195556 | A1 | 7/2017 | Emi et al. | |
| 2017/0222758 | A1* | 8/2017 | Saito | H04N 25/60 |
| 2019/0200844 | A1* | 7/2019 | Shelton, IV | H04L 63/123 |
| 2019/0297276 | A1* | 9/2019 | Sachdev | G16H 30/40 |
| 2020/0160057 | A1* | 5/2020 | Roxas | G06F 3/167 |
| 2023/0010235 | A1* | 1/2023 | Koch | A61B 1/0002 |
| 2023/0127774 | A1* | 4/2023 | Fuerst | A61B 1/000094 725/116 |

FOREIGN PATENT DOCUMENTS

| | | | |
|---|---|---|---|
| JP | 2003-57076 | A | 2/2003 |
| JP | 2011-244884 | A | 12/2011 |
| JP | 2021-090651 | A | 6/2021 |
| WO | 2015/182751 | A1 | 12/2015 |

* cited by examiner

MEDICAL IMAGE PROCESSING SYSTEM FOR DETECTING FAILURE AND METHOD FOR OPERATING THE SAME

CROSS-REFERENCE TO RELATED APPLICATIONS

This application claims priority under 35 U.S.C § 119(a) to Japanese Patent Application No. 2022-048170 filed on 24 Mar. 2022. The above application is hereby expressly incorporated by reference, in its entirety, into the present application.

BACKGROUND OF THE INVENTION

1. Field of the Invention

The present invention relates to a medical image processing system and a method for operating the same.

2. Description of the Related Art

In a medical device, such as an endoscope, a system that automatically detects an abnormality, such as failure of equipment, and stores the abnormality as an error log is generally used. In the error log, in addition to the classification or date and time of occurrence of the abnormality, the setting of the equipment, a processing status of a program, a communication status between modules, or the like at the abnormality occurrence are recorded. The fact that the abnormality, such as failure, occurs and the occurrence status can be ascertained by the error log. In detection of failure or the like by the error log, it is difficult to specify the specific content of failure or the cause of occurrence of failure. For this reason, it is desired to ascertain the specific content of failure using data other than the error log.

Specifically, in JP1993-5633A (JP-H5-5633A), examination is performed on a plurality of state signals representing an operating state of equipment. Detection is made that the state signal is outside an allowable range, and time at which the detection is made, an elapsed time from activation, and subsequent states are recorded. The type of the abnormality is displayed by a lamp, voice, or the like. In JP2003-57076A (corresponding to US2003/033062A1), an abnormality is detected from data indicating an operational state of equipment, and the operational state is recorded along with the type of the detected abnormality. Determination is made whether or not the abnormality is determined as failure, and recorded data is erased in a case where the abnormality that is not determined as failure is detected.

SUMMARY OF THE INVENTION

In JP1993-5633A (JP-H5-5633A), abnormality detection is performed using the state signal of the equipment, and in JP2003-57076A, determination is made whether or not an abnormality is a type that temporarily occurs at the time of an extremely high load and is highly likely to be self-recovered over time. In JP1993-5633A (JP-H5-5633A) and JP2003-57076A, the signal regarding the operating state of the equipment is acquired, abnormality detection, recording, and determination are performed, and the type of the abnormality is determined. Even though determination can be made to be not an abnormality due to failure, such as a temporary high load due to external noise, it is difficult to determine failure or to specify the cause of failure.

In equipment with size restriction, such as an endoscope, a dedicated sensor for detecting failure cannot be mounted, and cost is required. In a case where all data obtained from examination results are analyzed, a lot of labor is required for a user and it is not efficient. In addition, the capacity of a data storage region in an endoscope system is not always sufficient, and it is inefficient to constantly store data. For this reason, in the detection of failure from examination results obtained from normal examination equipment and recording to external equipment, it is desired to confirm failure contents and to specify failure causes efficiently.

An object of the present invention is to provide a medical image processing system and a method for operating the same capable of detecting an abnormality of equipment due to failure and of recording a detection result for each failure to external equipment to analyze a failure cause with efficiency without using a dedicated sensor for detecting failure.

A medical image processing system of the present invention comprises an external device having a processor, and an endoscope system, in which the processor is configured to acquire a real-time medical video image from the endoscope system during endoscopy, receive a trigger signal having information regarding failure occurrence created based on a failure scene of the medical video image from the endoscope system, temporarily store the medical video image in the external device, extract a failure video image having the failure scene from the temporarily stored medical video image based on a reception timing of the trigger signal in the external device, and store a failure video image in a main storage region of the external device.

It is preferable that the processor is configured to determine a start timing of the extraction based on the reception timing, and extract a failure video image including scenes before and after the reception timing in time series, from the medical video image.

It is preferable that the processor is configured to set a restriction period of the trigger signal after the reception of the trigger signal, and not start the extraction in a case where the trigger signal is received in the restriction period.

It is preferable that the processor is configured to set an upper limit number for the number of executions of the extraction.

It is preferable that the processor is configured to temporarily store the failure video image, and to sort the failure video image to be stored.

It is preferable that the processor is configured to perform the sorting based on a type of failure and an order of the reception timing.

It is preferable that the processor is configured to calculate an importance of the failure video image based on the information regarding the failure occurrence, and perform the sorting based on the importance.

It is preferable that the processor is configured to calculate the importance based on visibility of failure or a degree of seriousness of failure.

It is preferable that the processor is configured to calculate the importance based on a type of an endoscope.

It is preferable that the processor is configured to perform the sorting of the temporarily stored failure video image and the failure video image newly created by the extraction in an either-or format.

It is preferable that the processor is configured to perform processing at the extraction such that deletion or browsing of personal information included in image information of the medical video image is disabled.

It is preferable that the processor is configured to temporarily store the medical video image in a non-volatile memory.

It is preferable that the processor is configured to sort the failure video image temporarily stored in the non-volatile memory regardless of an end status of the endoscopy.

It is preferable that the processor is configured to set a different identifier to each failure video image at the extraction of the failure video image, confirm the identifier of the failure video image stored in the main storage region, and delete the failure video image having the same identifier as the confirmed identifier from the non-volatile memory.

A method for operating a medical image processing system that includes an external device having a processor, and an endoscope system, of the present invention comprises a step of acquiring a real-time medical video image from the endoscope system during endoscopy, a step of receiving a trigger signal having information regarding failure occurrence created based on a failure scene of the medical video image from the endoscope system, a step of temporarily storing the medical video image, a step of extracting a failure video image having the failure scene from the temporarily stored medical video image based on a reception timing of the trigger signal, and a step of storing the failure video image in a main storage region.

According to the present invention, it is possible to detect an abnormality of equipment due to failure and record a detection result of each failure to external equipment to analyze a failure cause with efficiency without using a dedicated sensor for detecting failure.

Figure 4:
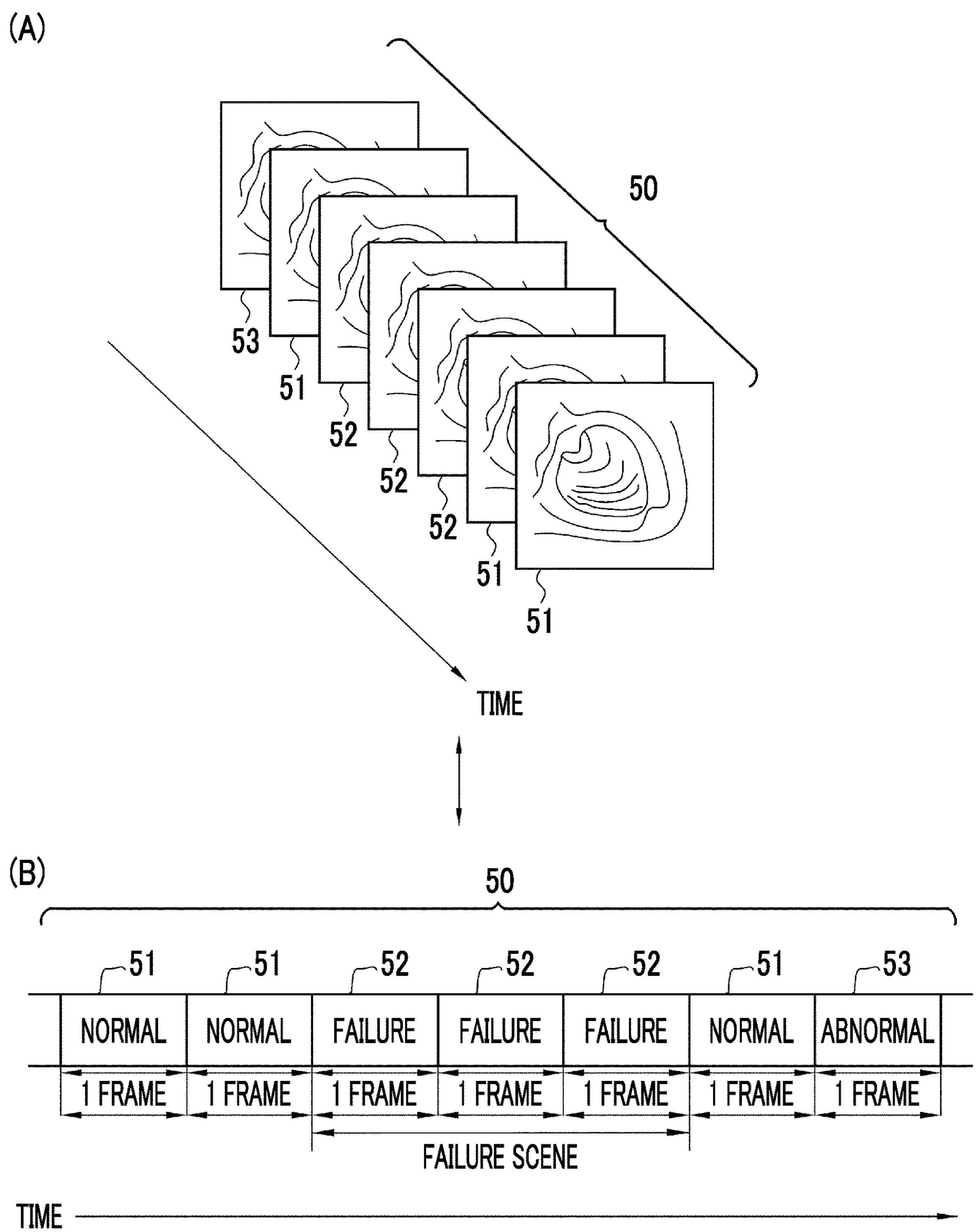

(A) and (B) of FIG. 4 is an explanatory view of a medical video image subjected to failure detection processing.

Figure 5A:
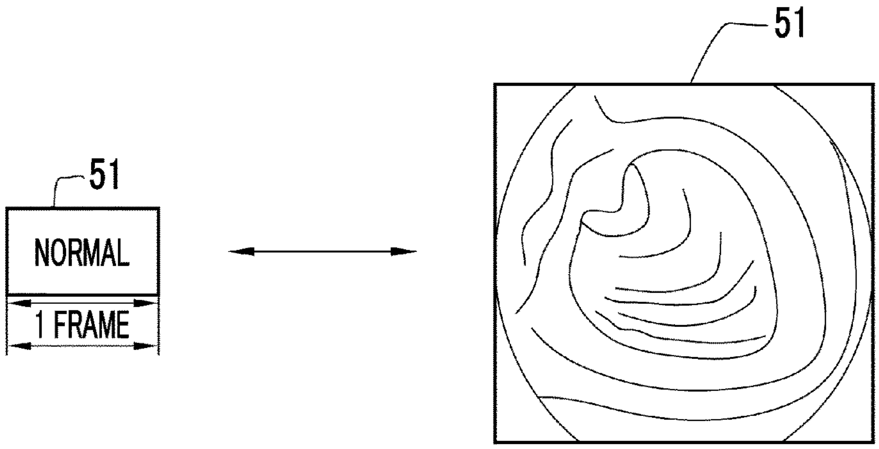
Figure 5B:
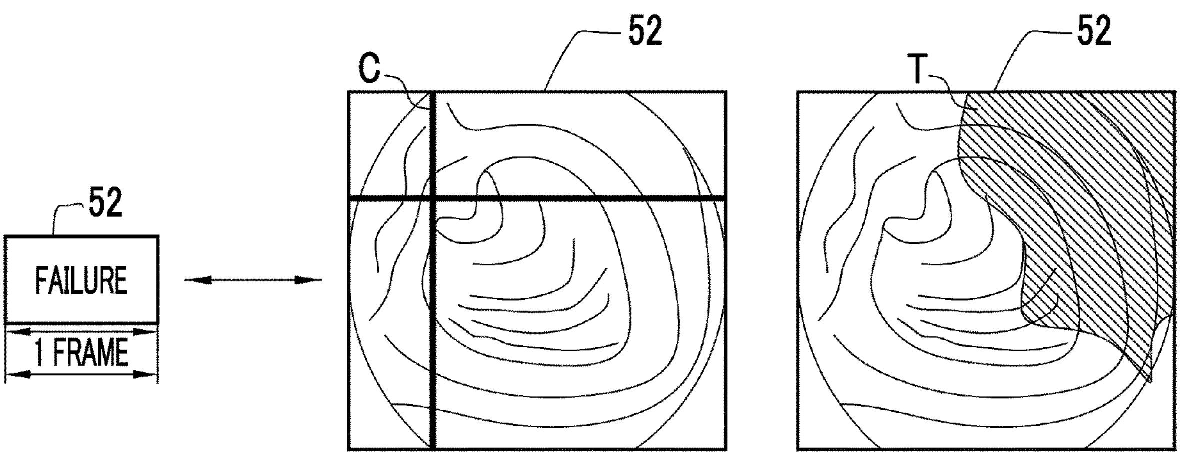
Figure 5C:
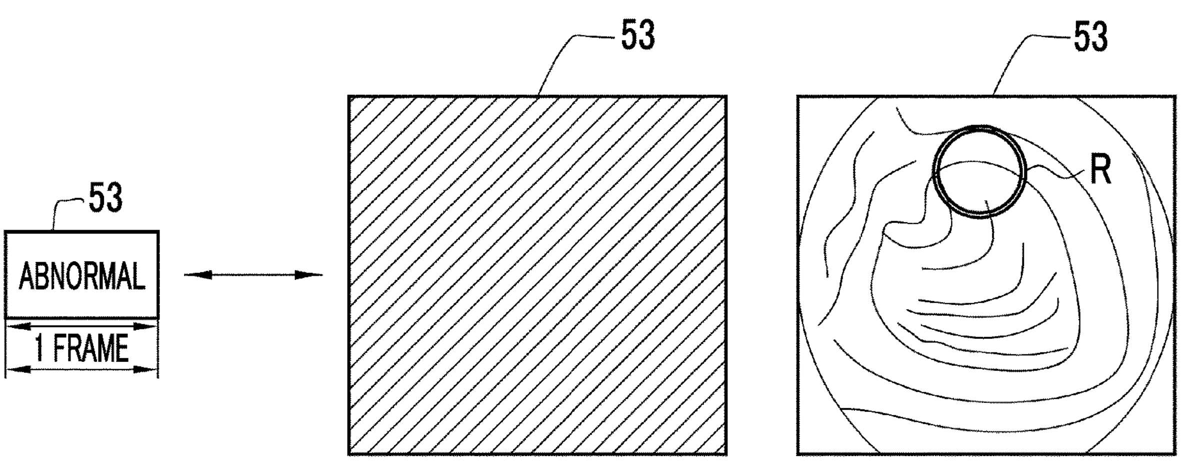

FIGS. 5A, 5B, and 5C are explanatory views of each frame image that is detected by the failure detection processing.

Figure 6:
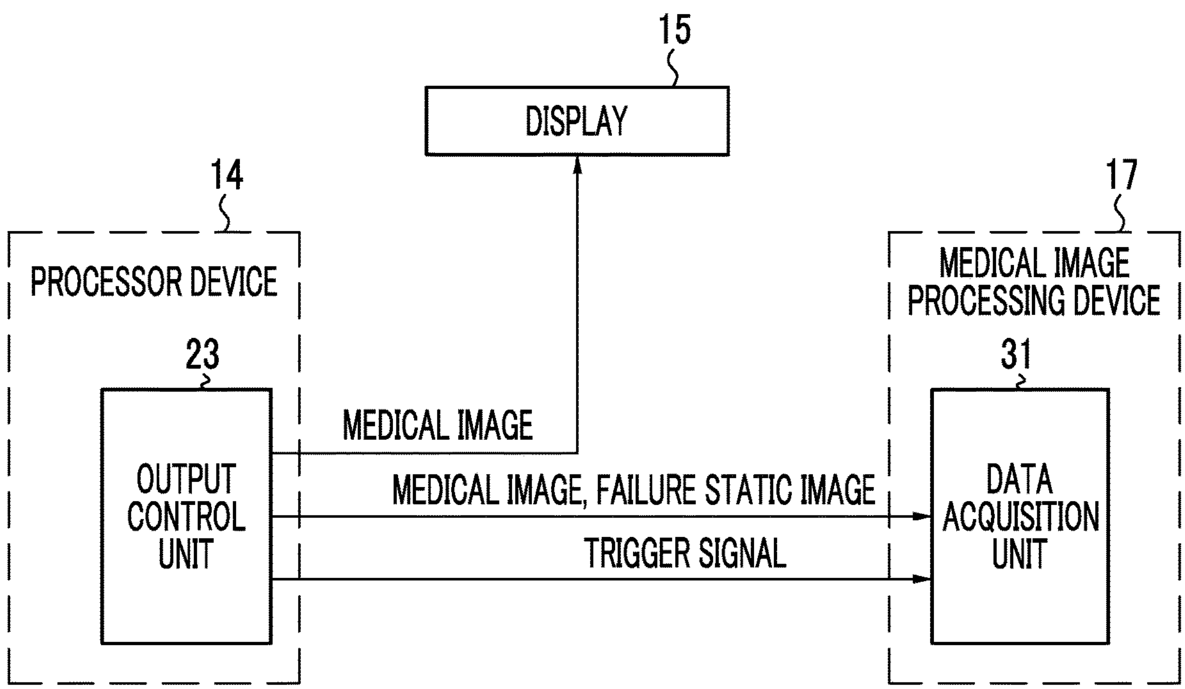

FIG. 6 is an explanatory view of data that is transferred from the processor device to the medical image processing device.

Figure 7:
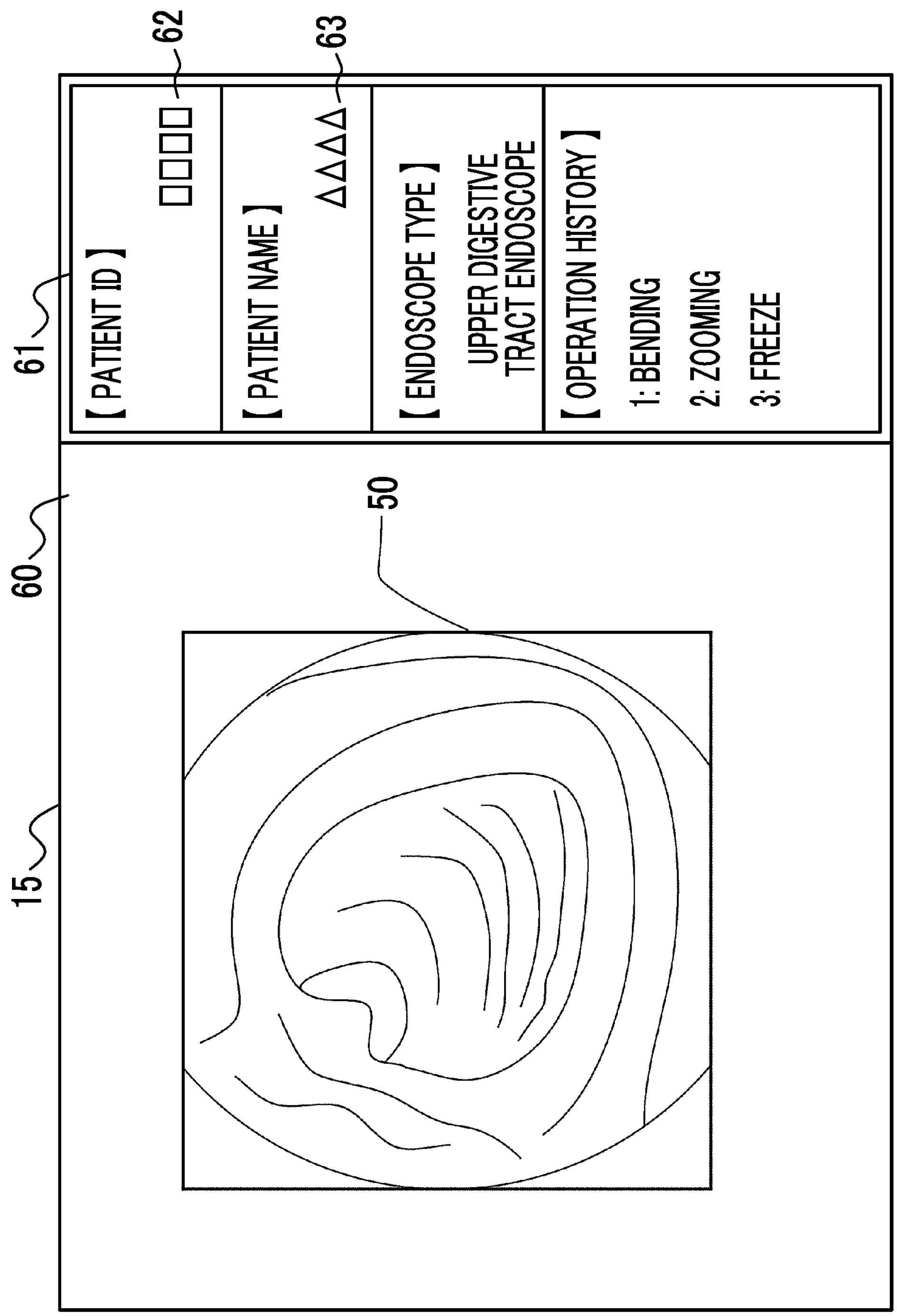

FIG. 7 is an image diagram in which a reproduction screen of the medical video image is displayed.

Figure 8:
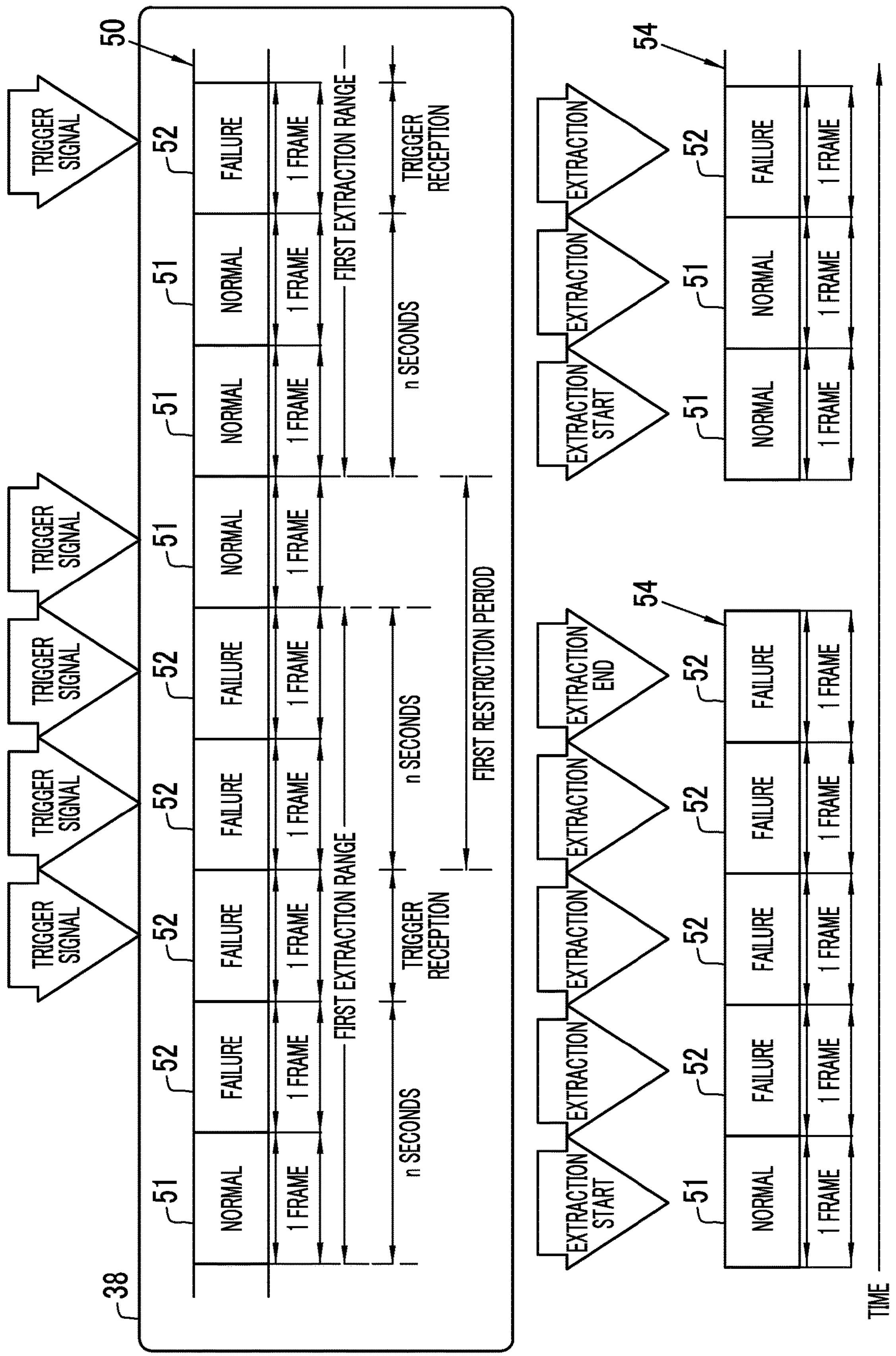

FIG. 8 is an explanatory view of extracting a failure video image in a first extraction range by a trigger signal.

Figure 9:
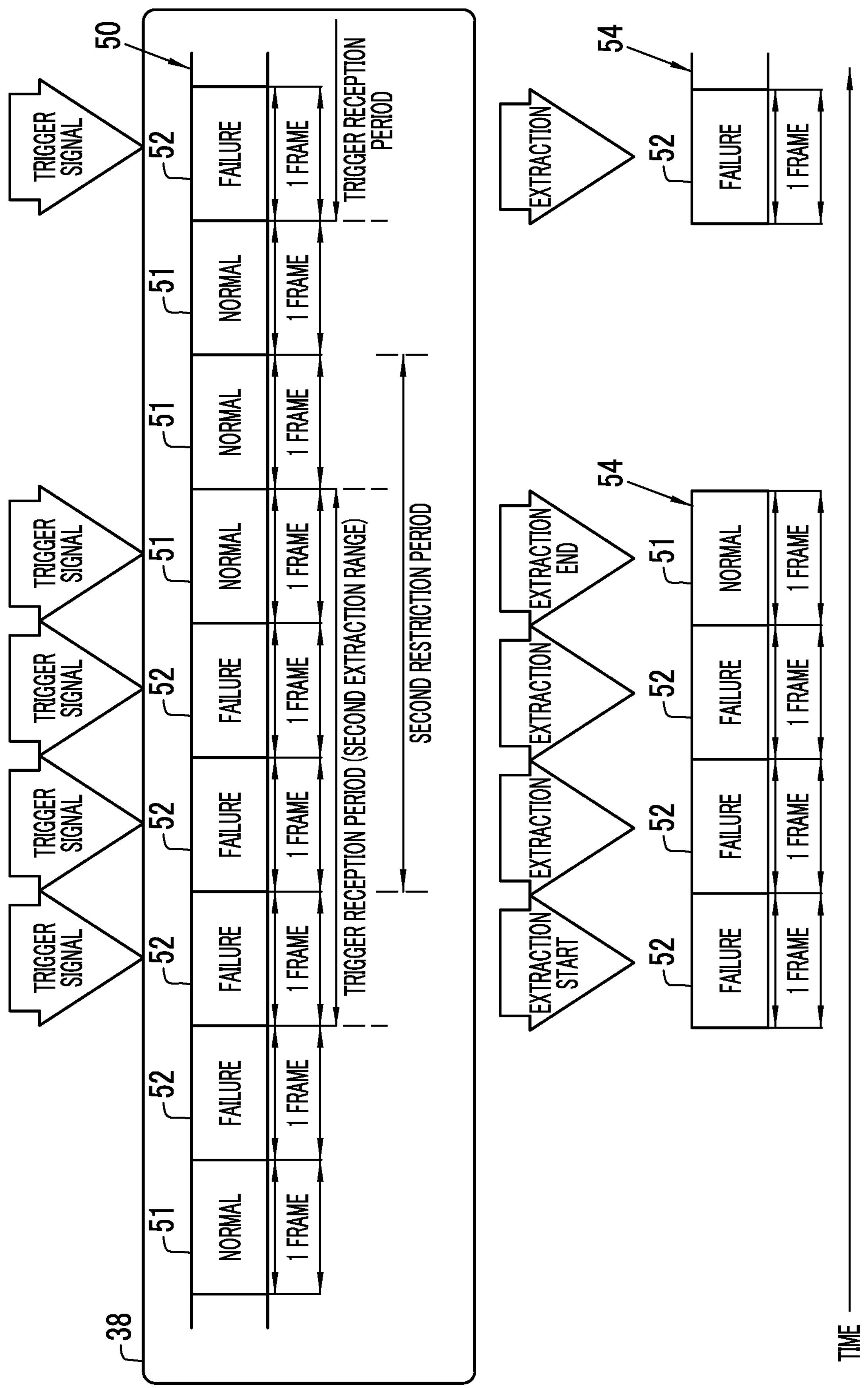

FIG. 9 is an explanatory view of extracting a failure video image in a second extraction range by a trigger signal.

Figure 10:
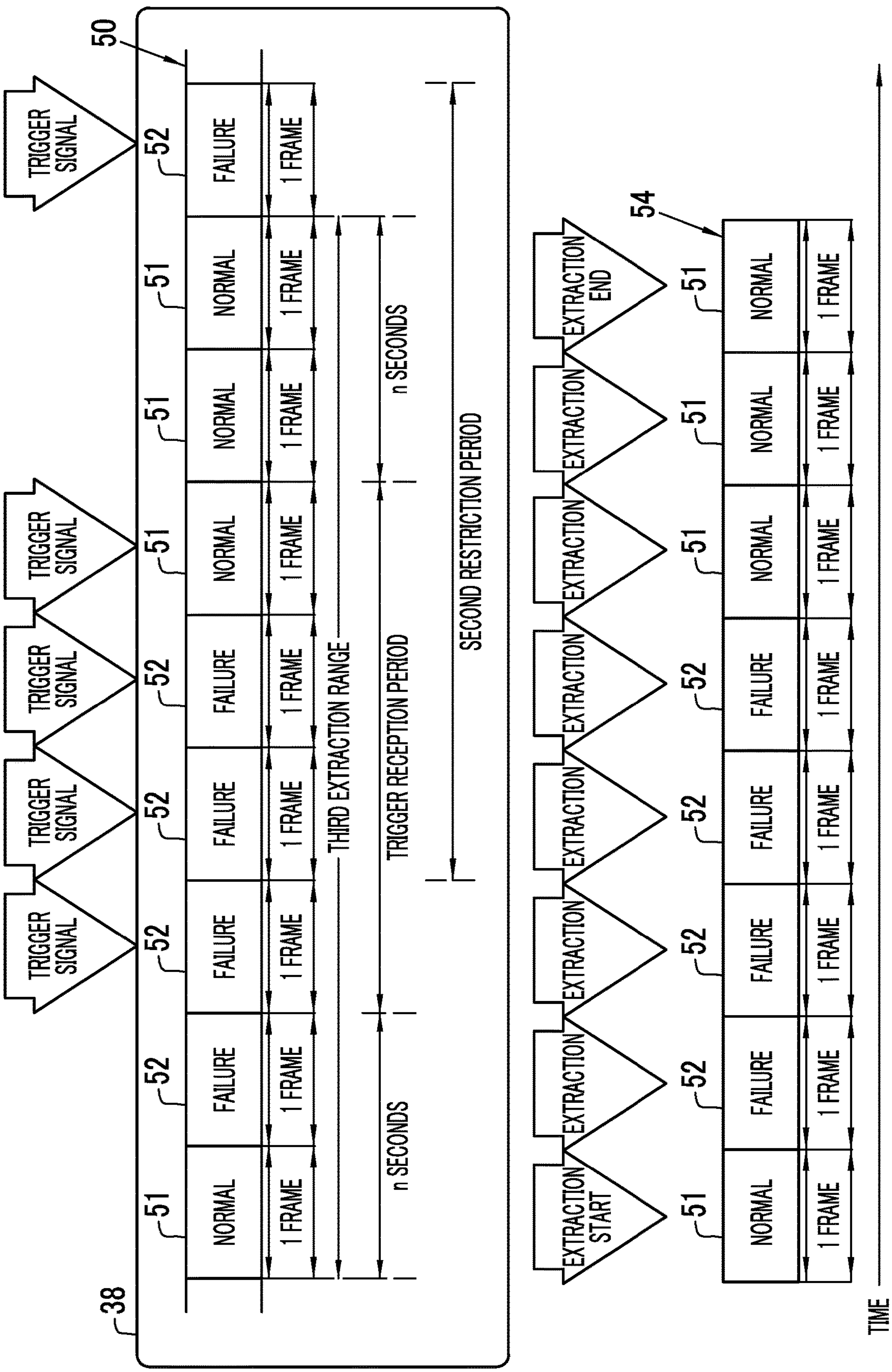

FIG. 10 is an explanatory view of extracting a failure video image in a third extraction range by a trigger signal.

Figure 11:
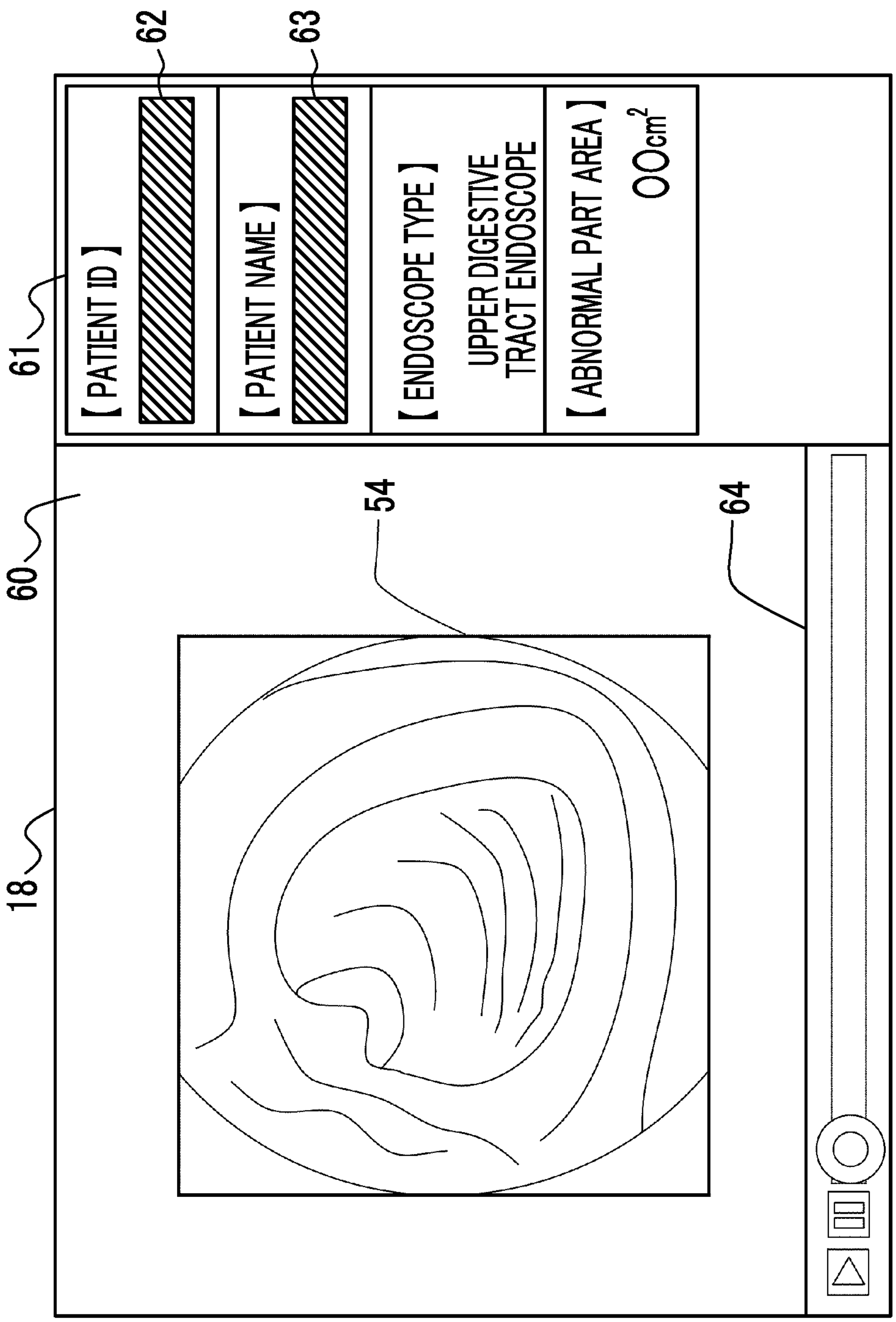

FIG. 11 is an image diagram in which a failure video image is displayed on a screen.

Figure 12:
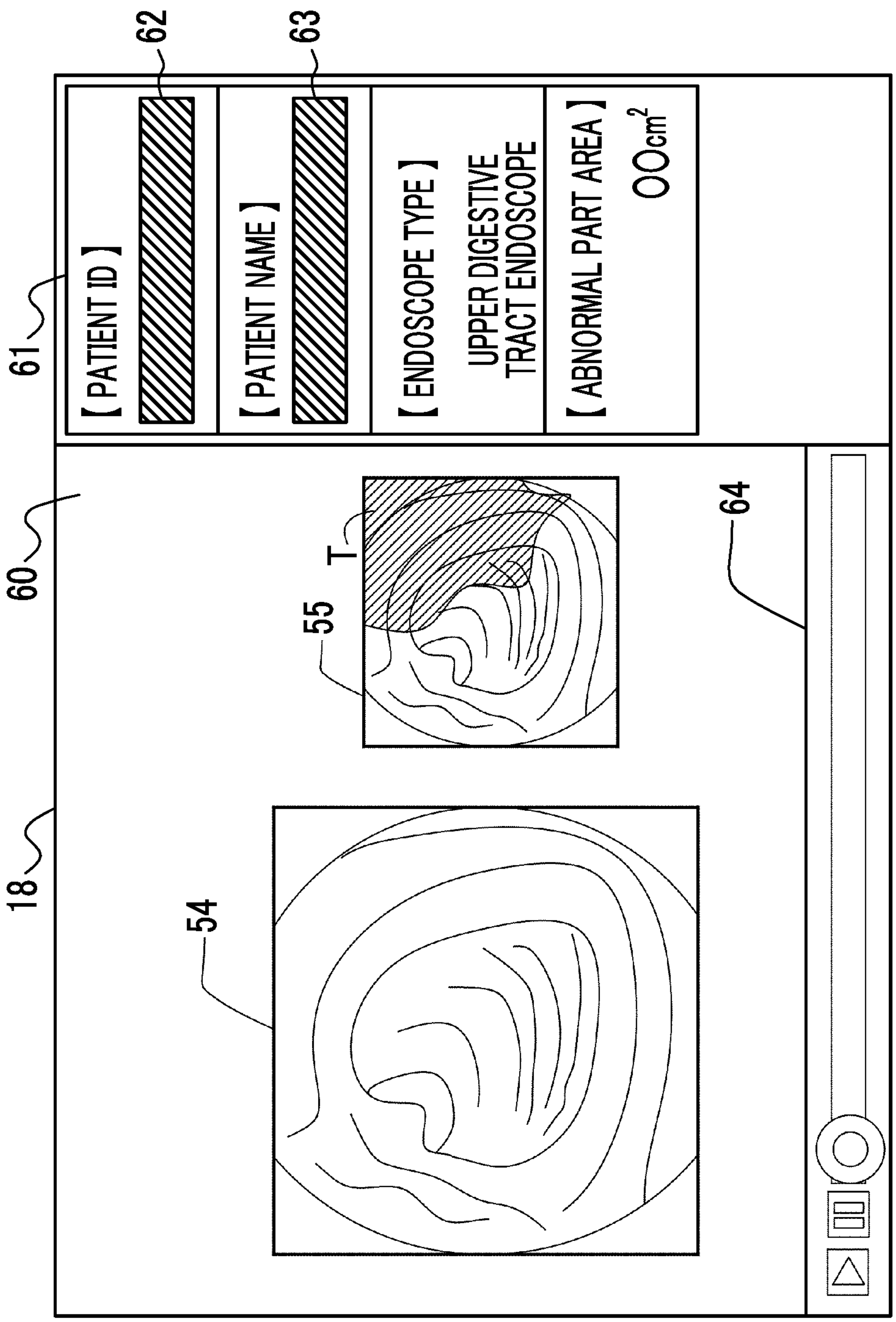

FIG. 12 is an image diagram in which a failure video image and a failure static image are displayed on the screen.

Figure 13:
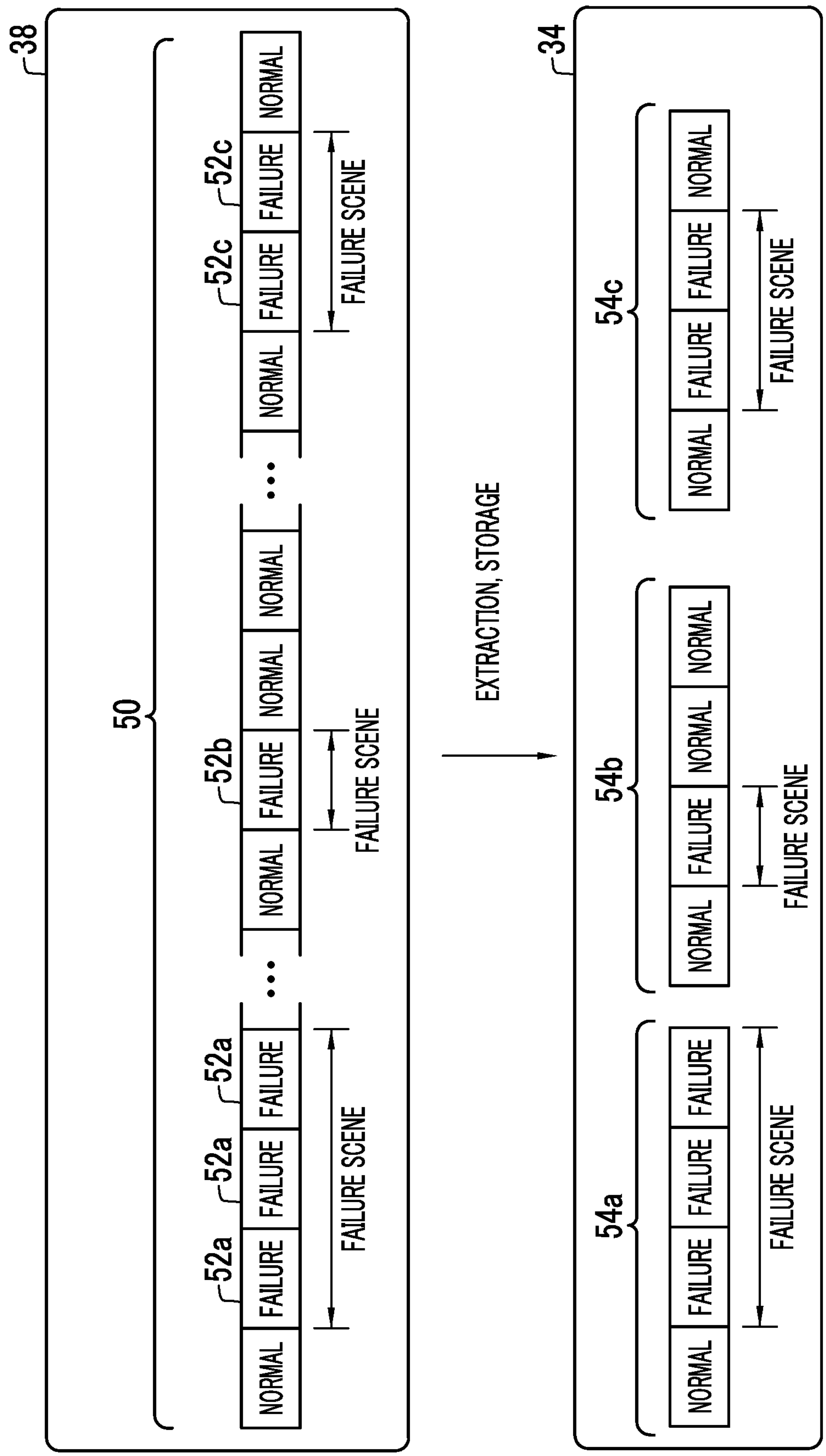

FIG. 13 is an explanatory view of a case where extracted failure video images are stored without being sorted.

Figure 14:
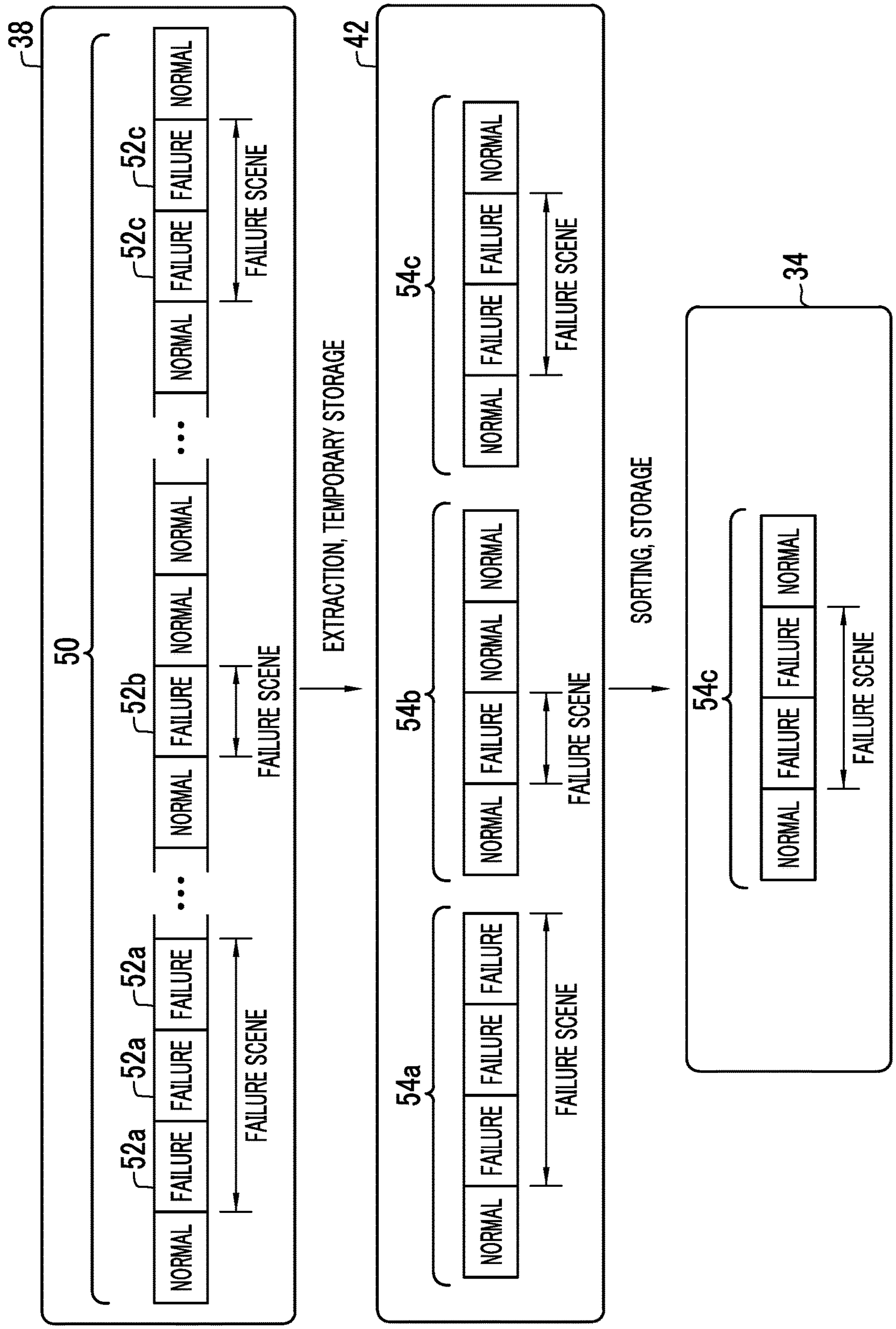

FIG. 14 is an explanatory view of a case where extracted failure video images are sorted and stored.

Figure 15:
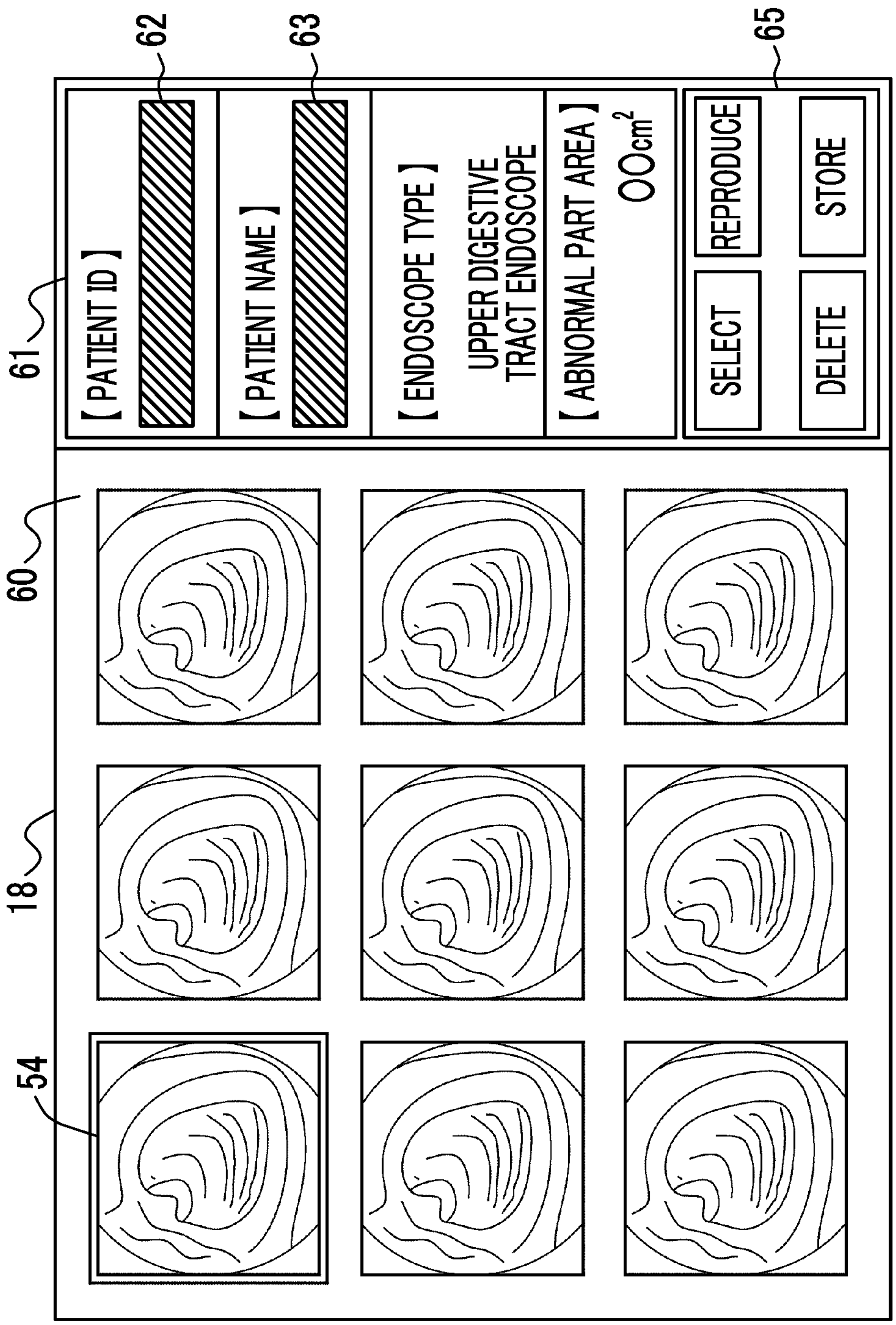

FIG. 15 is an image diagram in which failure video images are displayed as thumbnails.

Figure 16:
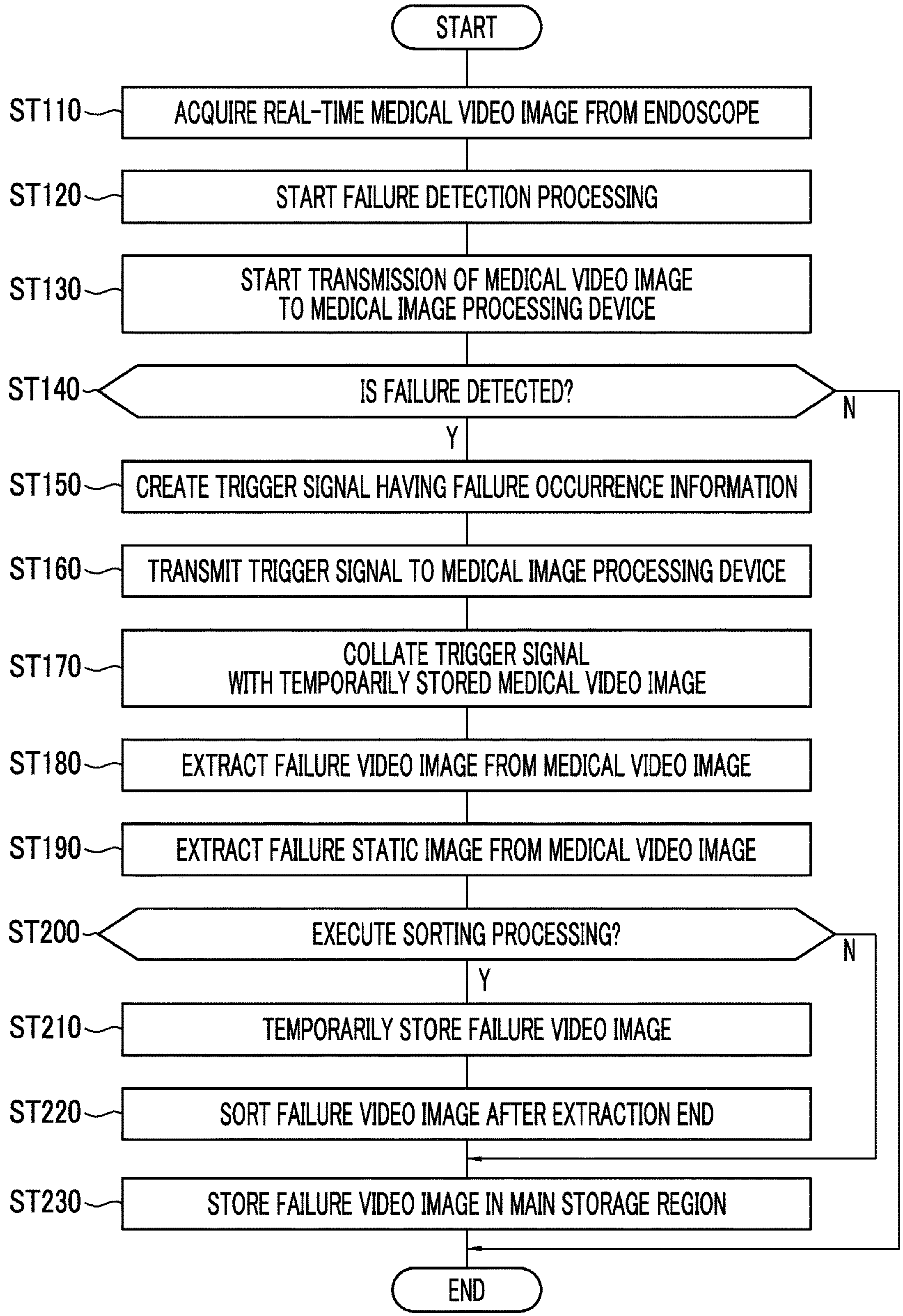

FIG. 16 is a flowchart illustrating a series of flow of processing of the present invention.

Figure 17:
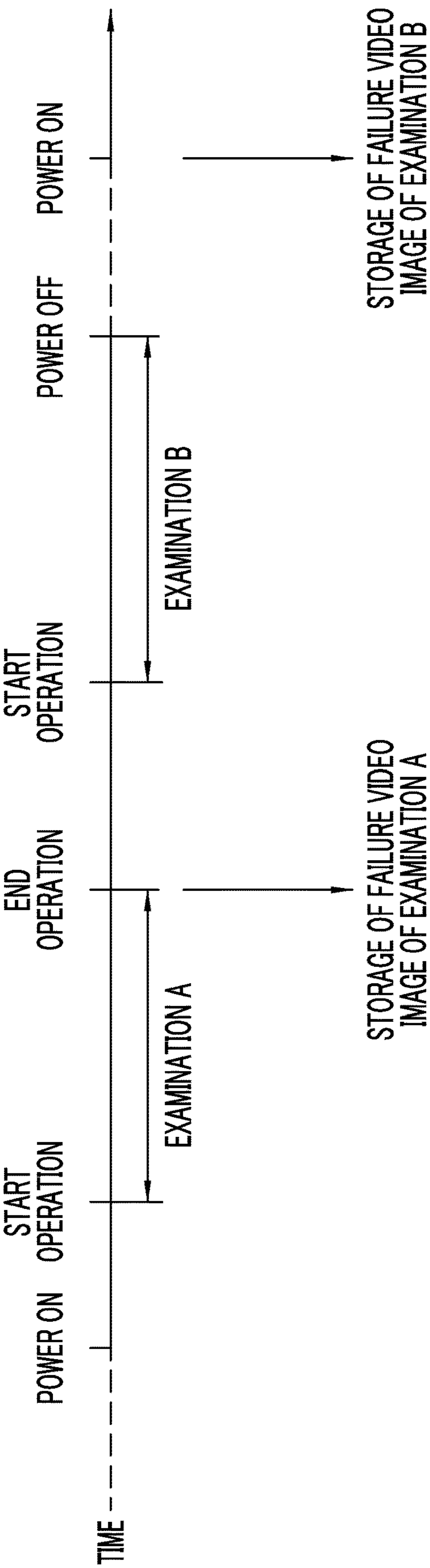

FIG. 17 is an explanatory view of temporarily storing a failure video image in a non-volatile memory in a second embodiment.

Figure 18:
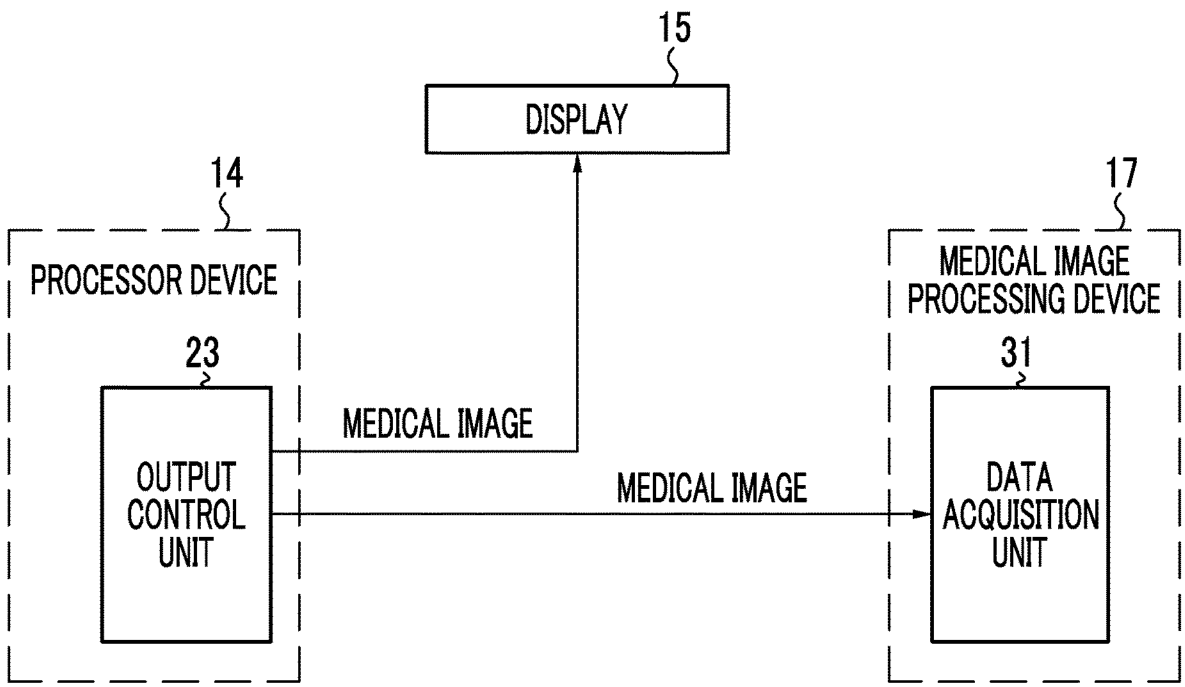

FIG. 18 is an explanatory view of data that is transferred from the processor device to the medical image processing device in a third embodiment.

Figure 19:
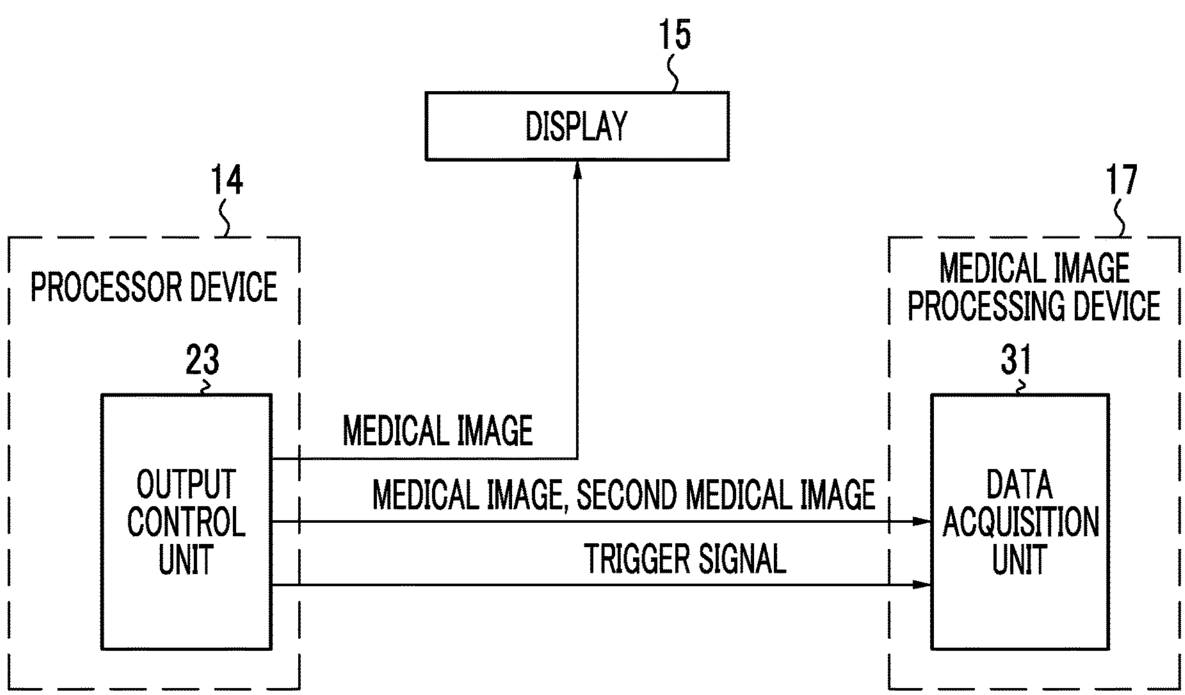

FIG. 19 is an explanatory view of data that is transferred from the processor device to the medical image processing device in a fourth embodiment.

DESCRIPTION OF THE PREFERRED EMBODIMENTS

First Embodiment

Figure 1:
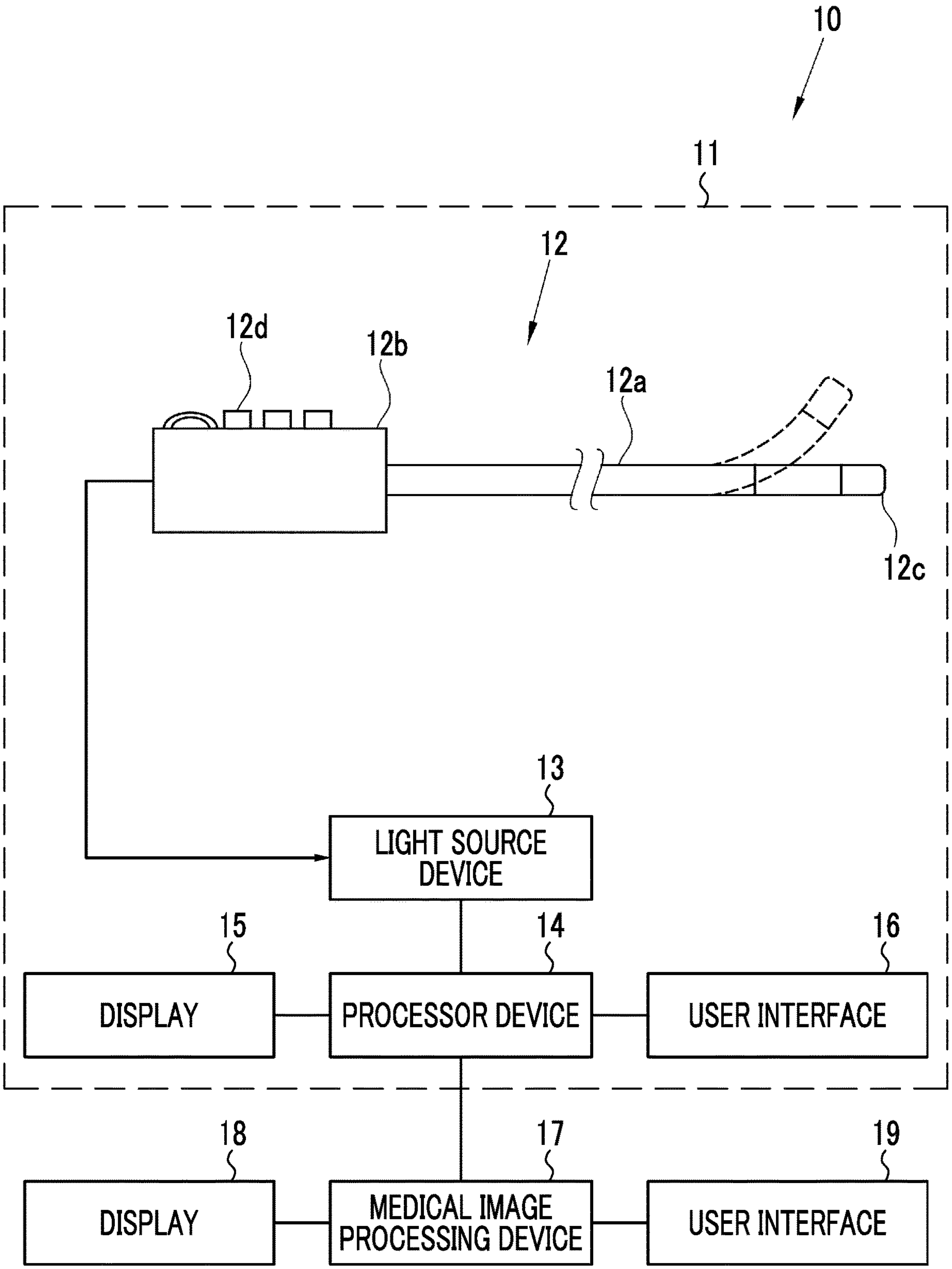
FIG. 1 is an explanatory view showing the configuration of a medical image processing system.

FIG. 1 is a diagram showing the configuration of a medical image processing system 10 having an endoscope system 11 of an embodiment of the present invention. The medical image processing system 10 has the endoscope system 11, a medical image processing device 17, a display 18, and a user interface (UI) 19, and the endoscope system 11 has an endoscope 12, a light source device 13, a processor device 14, a display 15, and a user interface (UI) 16. The processor device 14 is electrically connected to the light source device 13, the display 15, the user interface 16, and the medical image processing device 17. The medical image processing device 17 is electrically connected to the display 18 and the user interface 19. In the processor device 14 and the medical image processing device 17, a program regarding processing, such as image processing, is stored in a memory (not shown) for a program. The medical image processing device 17 is an external device not included in the endoscope system 11 that picks up a medical video image by endoscopy.

The endoscope 12 has an insertion part 12*a* that has an elongated shape and is inserted into a body of a patient to acquire a video image, and an operating part 12*b* that receives a user operation, such as bending of the insertion part 12*a*, or zooming in acquiring a video image, or a freeze operation to acquire a static image. The freeze operation is realized by depression of a freeze button 12*d* in the operating part 12*b*. At a distal end of the insertion part 12*a*, a distal end part 12*c* that has an imaging function and in which irradiation of illumination light or protrusion of a treatment tool is performed is provided.

The light source device 13 is optically connected to the endoscope 12 and supplies illumination light to the endoscope 12 in the endoscopy. The display 15 displays an image acquired by the processor device 14. The user interface 16 is an input device that performs an input or the like to the processor device 14, and uses a keyboard or a mouse, a foot pedal, a gesture recognizer, a voice recognizer, and the like. An input may be performed using input means provided in medical equipment, such as a switch of the endoscope 12, as well as the user interface 16. The image includes a video image, a static image, and a frame image composing a video image.

In imaging of the endoscopy, unless otherwise particularly designated, white light is used as illumination light, a video image signal of 60 frames a second (60 frame per second (fps)) is acquired, and an imaging time is recorded. It is preferable that the time is counted in units of one hundred of a second in a case where the video image signal is 60 fps.

The medical image processing device 17 is equipment that can transmit and receive data to and from the processor device 14, and receives data of a medical video image and failure information. In the medical image processing device 17, temporary storage of the received medical video image or extraction and storage of a failure video image using the failure information are performed. In the storage, an internal solid state drive (SSD) is preferably used. Instead of the SSD, a recording medium, such as a universal serial bus (USB) memory or a hard disk drive (HDD), may be used.

Figure 2:
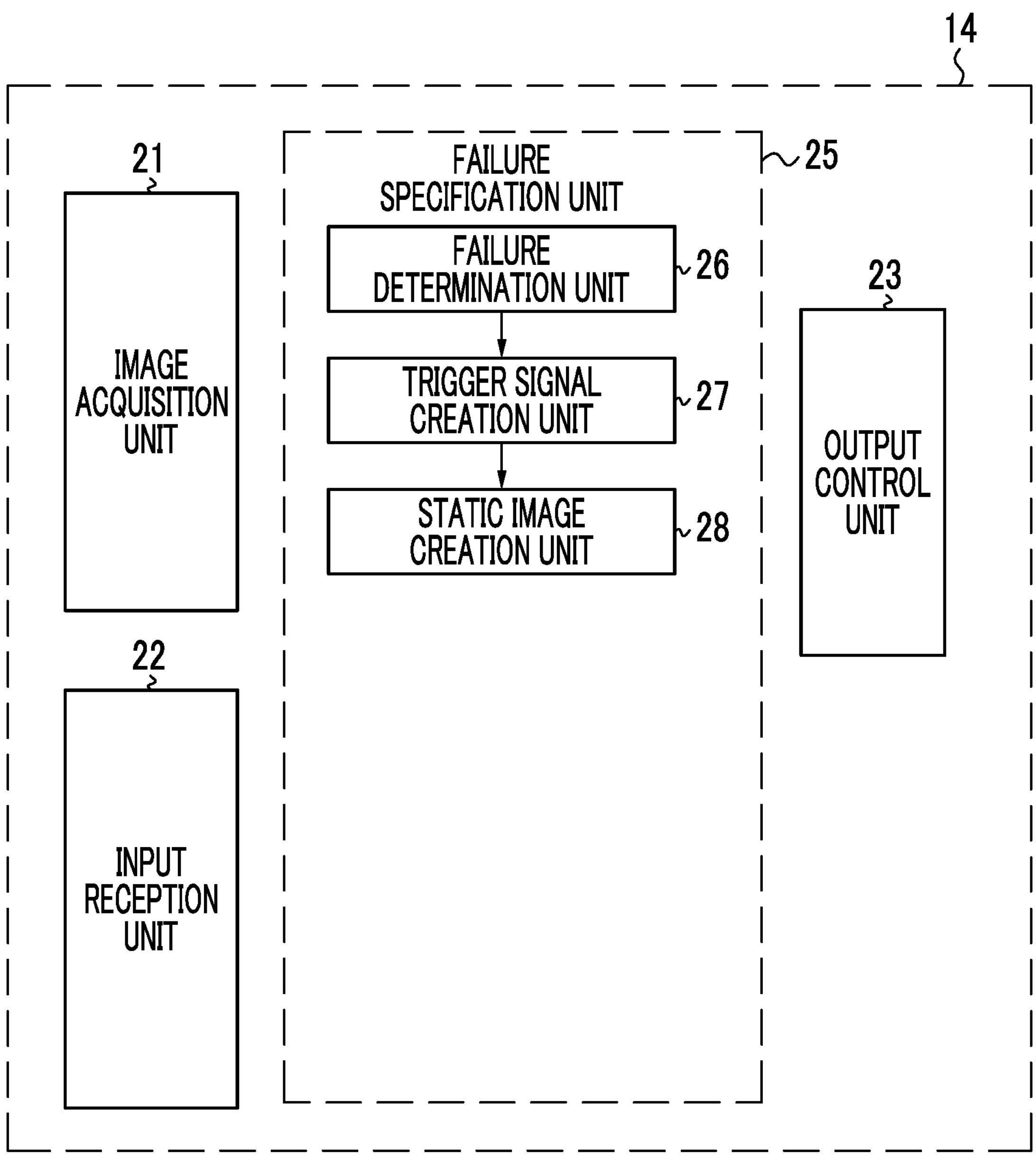
FIG. 2 is a block diagram showing the configuration of a processor device.

As shown in FIG. 2, in the processor device 14, the program in the memory for a program is operated by a central control unit (not shown) configured with a processor for image control, whereby functions of an image acquisition unit 21, an input reception unit 22, an output control unit 23, and a failure specification unit 25 are realized. With the realization of the function of the failure specification unit 25, functions of a failure determination unit 26, a trigger signal creation unit 27, and a static image creation unit 28 are realized.

The processor device 14 acquires a medical video image or a static image picked up by the endoscope 12 in real time, and executes failure detection processing and display on the display 15. A trigger signal having failure information, such as the type of failure detected by the failure detection processing, is transmitted to the medical image processing device 17.

The image acquisition unit 21 receives data of the medical video image or the like picked up by the endoscope 12. The acquired medical video image is transmitted to the output control unit 23 and the failure specification unit 25. The input reception unit 22 is connected to the user interface 16. The output control unit 23 performs control for displaying the medical video image on the display 15 and control for transmitting the medical video image to the medical image processing device 17.

Figure 3:
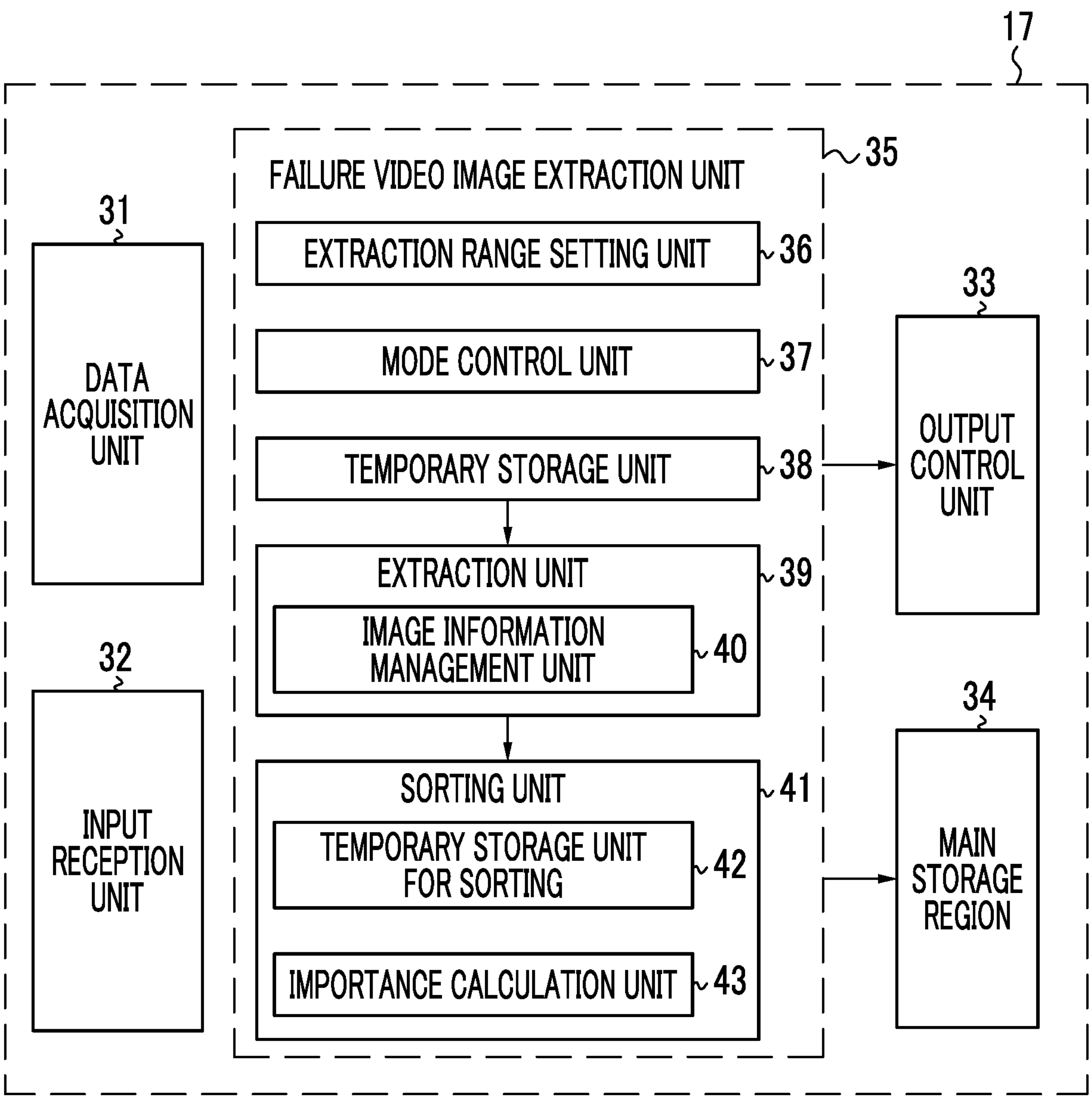
FIG. 3 is a block diagram showing the configuration of a medical image processing device.

As shown in FIG. 3, in the medical image processing device 17, the program in the memory for a program is operated by a central control unit (not shown) configured with a processor for image control, whereby functions of a data acquisition unit 31, an input reception unit 32, an output control unit 33, a main storage region 34, and a failure video image extraction unit 35 are realized. With the realization of the function of the failure video image extraction unit 35, functions of an extraction range setting unit 36, a mode control unit 37, a temporary storage unit 38, an extraction unit 39, and a sorting unit 41 are realized. In the extraction unit 39, a function of an image information management unit 40 is included, and in the sorting unit 41, functions of a temporary storage unit 42 for sorting and an importance calculation unit 43 are included.

The failure detection processing and the creation of the trigger signal that are executed by the processor device 14 will be described. In the failure determination unit 26, the failure detection processing is executed on the medical video image picked up by the endoscope 12, and detection of the presence or absence of failure of the endoscope 12 or determination of the type of failure is performed. In the trigger signal creation unit 27, the trigger signal that has information of a frame image having failure determined by the failure determination unit 26 or failure information, and is provided with a trigger function of causing the medical image processing device 17 to start the extraction processing is created.

The failure determination unit 26 executes the failure detection processing in real time during the endoscopy. In a case where the endoscopy starts, the image acquisition unit 21 receives one or a small number of frame images and inputs the frame images to the failure specification unit 25. The frame image input to the failure specification unit 25 are sequentially subjected to the failure detection processing by the failure determination unit 26, and a failure scene is detected.

As shown in FIG. 4, failure detection processing is executed on a temporally continuous medical video image 50 obtained by imaging the inside of a living body will be described. In the failure determination unit 26, the type of each frame composing the medical video image 50 is classified by the failure detection processing. (A) of FIG. 4 shows a part of a temporally continuous frame image group composing the medical video image 50, and in the failure detection processing, the frame images are sorted into a normal frame image 51 with no failure, a failure frame image 52 having an abnormality due to failure, and a failure-free abnormal frame image 53 that is abnormal but is not failure. With the sorting, information of the failure frame image 52 is transmitted as the trigger signal to the medical image processing device 17. The medical video image 50 acquired by the processor device 14 is not a video image file, and is a frame image group that is being picked up in real time.

(B) of FIG. 4 shows the same frame image group as in (A) of FIG. 4, and each rectangle represents one frame image. With the failure detection processing, a failure scene that is composed of a plurality of failure frame images 52 of the same failure in the medical video image 50 is specified. That is, the failure frame images 52 that have the same type of failure or the same feature shown in the image and are continuous are discriminated as one failure scene. In (B) of FIG. 4, although three continuous frames compose a failure scene, the number of frame images composing an actual failure scene is several tens or more and is enormous. The failure frame image 52 of only one frame, instead of continuous frames, may be discriminated as a failure scene. The failure frame images 52 of the same failure that are not completely continuous but have the same failure detected at a given frequency or more, for example, 80 percent or more may be determined as one failure scene. Extraction processing of a failure video image described below is executed for each failure scene, and the initial failure frame image 52 in the failure scene is a trigger signal reception timing by the trigger signal and is a starting point in the extraction processing.

In the failure detection processing, failure detection of detecting the failure frame images 52 from the frame images in the acquired medical video image 50, and failure determination of determining the type of failure, such as "disconnection", "scope dirt", or "lens damage", for the failure frame images 52, are performed. A determination result is transmitted to the trigger signal creation unit 27.

As shown in FIGS. 5A to 5C, the frame images classified by the failure detection processing have different features. As shown in FIG. 5A, the normal frame image 51 is a frame image in which an abnormality is not detected. As shown in FIG. 5B, the failure frame image 52 is a frame image in which failure of the endoscope 12, such as a state in which disconnection C with a vertical line or a horizontal line run is shown in the image due to "disconnection" or a state in which a part on the image is blotted out due to "scope dirt" regardless of an observation target and a non-lesion abnormal region T is included, is detected. As shown in FIG. 5C, the failure-free abnormal frame image 53 is a frame image that has an abnormality, such as a state in which a part or the whole of the image is not shown due to "external noise" or a state in which a lesion region R as a severe "lesion" is shown in the image, but is failure-free. The failure-free abnormal frame image 53 is handled in the same manner as the normal frame image 51 in the extraction processing.

The failure detection processing is executed using a function of a learned model necessary for the failure detection processing, for example. That is, the failure determination unit 26 has a computer algorithm comprising a neural network that performs machine learning, and performs detection of the presence or absence of failure of each frame image to the medical video image 50 input depending on learning contents or draws a specific inference with respect to determination of the type of failure in a case where failure occurs. In regard to an inference result, it is preferable that, in addition to a classification result of the frame image or the type of failure, information regarding a rate of coincidence with learning contents learned in advance is also acquired.

In the trigger signal creation unit 27, for each detected failure frame image 52, a trigger signal having the failure information and a trigger function are created. The failure information is information regarding the type of failure of the failure frame image 52, the scale of failure, the failure scene composed of the continuous failure frame images 52, and the like, and the trigger function is a trigger of starting the extraction processing of the failure video image from the medical video image 50 in the medical image processing device 17. Since the failure detection processing and the trigger signal creation are executed in real time, the trigger signal is created in conjunction with the detection of the failure frame image 52. The created trigger signal is transmitted to the medical image processing device 17 through the output control unit 23.

In the static image creation unit 28, a failure static image that is a static image of the failure frame image 52 detected by the failure detection processing is created. It is preferable that the failure static image is created at the same time with the trigger signal. The created failure static image is transmitted to the medical image processing device 17 through the output control unit 23. Only one initial failure static image may be created from the failure frame images 52 that are continuous and has the same type of failure.

As shown in FIG. 6, through the output control unit 23 of the processor device 14, the medical video image 50 is transferred to the display 15, and the medical video image 50 and the trigger signal are transferred to the medical image processing device 17. The transfer of data may be performed by wired communication or may be performed by wireless communication. In a case of the wired communication, transmission of the medical video image 50 using a digital visual interface (DVI) as a video image transmission line and transmission of the trigger signal using Recommended Standard 232 version C (RS232c) as a trigger transmission line may be performed or transmission of the medical video image 50 and the trigger signal to the medical image processing device 17 using a USB cable may be performed. Data transferred to the medical image processing device 17 is received by the data acquisition unit 31. Since the same medical video image 50 is transmitted to the display 15 and the medical image processing device 17, the medical video image 50 may be transmitted to the medical image processing device 17 through the display 15.

Since the medical video image 50 is picked up in real time, the transfer of data is constantly performed, but the trigger signal is created and transferred only in a case where failure is detected. Since the medical video image 50 that is transferred to the medical image processing device 17 does not have failure information, the failure frame image 52 is specified through collation with the trigger signal in the medical image processing device 17.

As shown in FIG. 7, the display 15 that configures the endoscope system 11 displays an image display region 60 where the medical video image 50 is reproduced and imaging contents can be confirmed, and an image information display field 61 where image information of the medical video image 50 reproduced is displayed. The image display region 60 during endoscopy performs real-time reproduction, and the image information that is displayed in the image information display field 61 is, for example, a patient ID 62, a patient name 63, an endoscope type, and an operation history. In FIG. 7, it is assumed that the patient ID 62 is "□□□□", the patient name is "ΔΔΔΔ", and the endoscope type is an "upper digestive tract endoscope". It is preferable that the operation history displays a history of operations on the operating part **12*b* in the endoscope 12** in a descending order. For example, it is preferable that the history of operations is displayed in such a format that a newest operation is a "bending" operation, a second newest operation is a "zooming" operation, and a third newest operation is a "freeze" operation.

The medical image processing device 17 that is an external device with respect to the endoscope system 11 performs extraction and storage of a failure video image based on the medical video image 50 and the trigger signal received in real time from the processor device 14. The medical image processing device 17 acquires the real-time medical video image 50 from the endoscope system 11 during endoscopy, temporarily stores the acquired medical video image 50 in the temporary storage unit 38, acquires the trigger signal having the trigger function of starting the extraction and the failure information created based on the failure scene, created by the endoscope system, and extracts a failure video image having a failure scene from the temporarily stored medical video image 50 based on the reception of the trigger signal, in the extraction unit 39. The extracted failure video image is stored in the main storage region 34 of the medical image processing device 17. The medical image processing device 17 also acquires the failure static image created by the static image creation unit 28.

Since the reception of the trigger signal is asynchronous with the reception of the medical video image 50, an error occurs between the trigger signal and a timing at which the medical image processing device 17 acquires the failure frame image 52 corresponding to the trigger signal. Since the trigger signal is created based on information detected from the medical video image 50, the trigger signal is liable to be delayed later than a corresponding frame of the medical video image 50. For example, it is preferable that the extraction is performed while including the error.

In the extraction range setting unit 36, an extraction range in extracting a failure video image is set before the start of the endoscopy. The extraction unit 39 executes the extraction processing following any extraction range among first to third set extraction ranges depending on the reception of the trigger signal. It is preferable that a start timing of extraction in the trigger function is determined based on information regarding a reception timing of the trigger signal in the medical image processing device 17, and a failure video image including scenes before and after the reception timing of the trigger signal in time series is extracted from the medical video image 50.

The extraction processing is executed based on the extraction range set by the extraction range setting unit 36. In the first extraction range, a group of a plurality of continuous frame images in a range within n seconds before and after the reception timing of the trigger signal as the scenes before and after the reception timing of the trigger signal is extracted. In the second extraction range, a range where the trigger signal having the same type of failure is continuous is extracted. In the third extraction range, continuous frame images in a range of a given period within n seconds before and after the second extraction range are extracted. It is preferable that the first extraction range is set in a case of unifying or reducing a recording time of failure video images, the second extraction range is set in a case of comparing a lot of failure video images, and the third extraction range is set in a case of comparing a failure scene with a normal scene.

It is preferable that the given period within the n seconds before and after the reception timing of the trigger signal in the first extraction range and the third extraction range is set to such an extent that comparison with the normal frame images 51 before and after failure occurrence can be performed and a storage is not pressed, for example, three seconds (n=3) or five seconds (n=5). It is preferable that the extraction range of the normal frame image 51 is determined based on the type of failure, a duration of failure, and an average area of an abnormal part in a frame image due to failure, determined by the failure detection processing. For example, in a failure scene where the duration is long or a failure scene where the type of failure is "disconnection", the value of n seconds, that is, the range of failure video images to be extracted is extended.

In a case of the second extraction range and the third extraction range, an upper limit of a recording range of each failure video image is set in advance. In a case where failure is not temporary and is not self-recovered, a case where a lot of time is required for self-recovery, or the like, the recording range of the failure video image is determined by the lapse of given time. For example, a point of time at which a failure scene is detected for five seconds is set to an end of a failure video image to be extracted. The given time is not limited to five seconds, and may be ten seconds or 30 seconds.

In the mode control unit 37, control regarding the extraction and storage of the failure video image is performed. In the mode control unit 37, a normal mode or a storage mode is set, and the storage mode is further classified into any of first to fourth storage modes depending on a condition and a method in extracting and storing a failure video image from the medical video image 50. It is preferable that the setting of the storage mode is set in advance before the endoscopy. In the normal mode, the real-time display of the acquired medical video image 50 on the display 15 or the display 18 and the storage of the medical video image 50 in the main storage region 34 of the medical image processing device 17 are performed.

In the first storage mode, all extracted failure video images are stored in the main storage region 34 without being sorted. In the second to fourth storage modes, the extracted failure video images are transmitted to the sorting unit 41 and are temporarily stored in a temporary storage region through the temporary storage unit 42 for sorting, and the failure video images that are stored in the main storage region 34 are sorted. The second storage mode performs sorting based on the type of failure and an order of failure detection, the third storage mode performs sorting based on the type of failure and an importance of failure, and the fourth storage mode performs sorting depending on user's selection. Details of extraction or sorting in each storage mode will be described below.

In the temporary storage unit 38, a real-time video image of the medical video image 50 transferred from the processor device 14 is stored in the temporary storage region. The temporary storage region is formed in a volatile memory or a non-volatile memory, and may be physically the same as the main storage region 34 in a case of the non-volatile memory. The medical video image 50 that records a whole medical examination may be only temporarily stored and may not be stored in the main storage region 34.

In the extraction unit 39, the trigger signal received from the data acquisition unit 31 is transferred, and a frame image group that is extracted as a failure video image based on the trigger signal is acquired from the temporary storage unit 38. A frame image corresponding to the failure information of the trigger signal, that is, the failure frame image 52 in the temporarily stored medical video image 50 is specified. The failure video image is extracted from the medical video image 50 following the trigger signal and the setting of the extraction range. It is preferable that the failure video image holds information regarding the trigger signal.

Since the trigger signal is transferred each time the failure frame image 52 is detected, the trigger signal is received in a large amount in each failure scene. The failure video image of each failure frame image 52 in the same failure scene, that is, a failure video image of the same failure scene does not need to be redundantly acquired. In a case where the failure video image is acquired redundantly, the amount of the extraction processing is enormous, and the capacity of the storage region is pressed. For this reason, it is preferable that, in a case where the extraction of the failure video image is started, extraction start in the same failure scene is restricted.

In the extraction processing, a restriction period of the trigger function during which start new extraction processing is not started is set for a given period after the reception of the trigger signal, and in a case where the trigger signal is received in the restriction period, the trigger function is not realized, and the failure information of the failure frame image 52 is received and collated with the medical video image 50. The extraction of the failure video image by the trigger function is realized again after the end of the restriction period. The restriction period starts immediately after the reception of the trigger signal, and ends at the same time as the end of the extraction range or when a given number of seconds have elapsed from the end.

As shown in FIG. 8, in the extraction processing of a case of the first extraction range, a first restriction period is set as the restriction period of the trigger function. In the first restriction period, only the acquisition of the failure information from the received trigger signal is performed. The first restriction period ends when a period within n seconds after the reception timing of the trigger signal that is the end of the first extraction range or the extraction range ends.

As shown in FIGS. 9 and 10, in the extraction processing of a case of the second extraction range and the third extraction range, a second restriction period is set as the restriction period of the trigger function. In the second restriction period, while new extraction is not started for the same type of failure, the failure information is acquired from the trigger signal, and the extension of the extraction range is received with the reception of the trigger signal that is continuous and has the same type of failure. The second restriction period ends at the same time with the determination of the extraction range or after the determination of the extraction range. As the trigger signal that has the same type and is continuous is continuously received, the second restriction period is extended.

In the image information management unit 40, the image information of the medical video image 50 and the failure information acquired from the trigger signal are managed.

The failure information is information regarding a state of failure, such as a non-lesion abnormal region T of the failure frame image 52, and is associated with the extracted failure video image 54. The failure information is, for example, the trigger signal reception timing, the type of failure, an area of the non-lesion abnormal region T due to failure, and a duration of the failure scene.

In the extraction processing, in addition to the extraction of the failure video image, edition of the image information other than the failure information is also performed. While the failure video image 54 is used for analysis of failure of the endoscope 12, a person who is responsible for analysis is a serviceman of a medical equipment manufacturer, not a user of the endoscope 12. For this reason, patient information included in the image information of the medical video image 50 needs to be not obtained from the failure video image 54. In the image information management unit 40, at the extraction processing, processing is performed such that deletion or browsing of the patient information, such as the patient ID 62 or the patient name 63, recorded in the medical video image 50 is disabled. In regard to the processing, mask processing, such as blotting-out of characters, or mosaicing of characters is performed.

Even in a case where the user who performs the endoscopy browses or analyzes the failure video image 54, in a case of creating data that is handled outside a network of a hospital, patient information is not left. In a case where the lesion region R is included in the failure frame image 52, lesion information, such as a detected lesion name, is also handled as patient information. For this reason, processing is performed such that deletion or browsing of the lesion information is also disabled at the extraction processing.

In a case where a lot of failure scenes are detected from the medical video image 50, a lot of time is required for the extraction processing or the sorting processing, and a lot of time is required until the acquisition or the confirmation of the failure video image 54. For this reason, it is preferable that an upper limit number of the number of executions of the extraction of the failure video image 54 is provided. In a case where the upper limit number is provided, the extraction is stopped in a case where the number of detections of failure reaches a set number of times, such as five or ten. For example, in a case where the upper limit number is set to five, after the failure video image 54 is extracted, the extraction is not executed even though the failure frame image 52 is detected. There is known a method in which, after the upper limit number is reached, specifically, the restriction period of the trigger function is set to be unrestricted, and the trigger signal itself is not received or the mode control unit performs switching from the storage mode to the normal mode to end of the failure detection processing. The upper limit number may be set for each type of failure. The upper limit number may be set to one, and discrimination may be made whether or not the endoscope 12 has failure.

In a case where the storage mode is the first storage mode, since sorting is not performed, and the failure video image 54 extracted by the extraction unit 39 is stored in the main storage region 34. In a case of the second storage mode to the fourth storage mode, since the sorting of the failure video image 54 to be stored is performed, the failure video image 54 is transmitted from the extraction unit 39 to the sorting unit 41 and is temporarily stored in the temporary storage unit 42 for sorting.

In the sorting unit 41, the sorting of the failure video image 54 is performed depending on a sorting criterion that is defined in each of the second to fourth storage modes. A failure scene that is highly likely to be beneficial to analysis of a failure cause can be narrowed down by performing the sorting. In regard to the sorting, at least one of comparison between failure scenes or failure information of the failure video images 54 or determination regarding whether or not a failure scene satisfies a criterion defined in each storage mode.

In a case of executing the sorting processing, the temporary storage unit 42 for sorting temporarily stores each failure video image 54 before the execution of the sorting processing. It is preferable that the sorting is performed after the extraction processing ends and all the failure video images 54 are temporarily stored. The temporary storage is realized by storing the failure video image in the temporary storage region (not shown) that is the volatile memory or the non-volatile memory in the medical image processing device 17, through the temporary storage unit 42 for sorting. In a case where the temporary storage region is the non-volatile memory, the failure video image may be temporarily stored in the same region physically as the main storage region 34.

In the importance calculation unit 43, the importance of each failure video image 54 is calculated. A way of representing the importance is, for example, percentage (%) or stepwise evaluation (high, middle, low). As the importance of the failure video image 54 is high, the failure video image 54 is highly likely to be beneficial to analysis of failure, or the like. The failure information for calculating the importance is acquired by the image information management unit 40 that stores the failure information of the trigger signal.

The importance is calculated using at least one of an order of the trigger signal reception timing, the type of failure, a frequency of failure occurrence, a degree of seriousness of failure, a degree of confidence of failure detection, visibility of failure, an influence, or the type of the endoscope 12. The degree of seriousness of failure can be calculated by the area, brightness of color, chroma saturation, color, an occurrence position, and the like of the non-lesion abnormal region T in the failure frame image 52. The visibility of failure can be calculated by a brightness difference between the non-lesion abnormal region T and a subject on a background. The type of the endoscope 12 includes an endoscope for treatment, an endoscope for diagnosis, an upper digestive tract endoscope, a lower digestive tract endoscope (colonoscope), a nasal endoscope, and the like.

The output control unit 33 performs control of display and the like of the failure video image 54 on the display 18. In a case of displaying the failure video image 54, confirmation of the failure scene and reference of the failure information or edition of image information including the failure information or a video image composition by the user, through the user interface 16 is received. The temporarily stored medical video image 50 may be output to and displayed on the display 15 or the display 18.

As shown in FIG. 11, the display 18 expands the image display region 60 where the failure video image 54 and the corresponding failure static image are displayed, the image information display field 61 where the image information including the failure information is displayed, and a video image reproduction tool bar 64 that performs display regarding a reproduction status of the failure video image 54. In the image display region 60, for example, the failure video images 54 can be reproduced in an order of the extraction and failure contents can be confirmed. The failure information that is displayed in the image information display field 61 is, for example, the type of failure, a failure scene time, the average area of the non-lesion abnormal region T, and the order of the trigger signal reception timing. At the extraction processing, the personal information included in the image information of the medical video image 50 is processed such that browsing is disabled. For example, in FIG. 7, the patient ID 62 displayed as "□□□□" and the patient name 63 displayed as "ΔΔΔΔ" are processed irreversibly such that character portions cannot be discriminated.

As shown in FIG. 12, the display 18 may display a failure static image 55 corresponding to the failure scene of the failure video image 54 in the image display region 60, in addition to the failure video image 54. Since the failure static image 55 shows the failure scene of the failure video image 54, confirmation and the like of the state of failure, for example, the non-lesion abnormal region T, can be performed.

In regard to the extraction processing in each storage mode described below, the extraction processing is executed in the first extraction range unless otherwise particularly designated. For example, continuous frame images within three seconds before and after a timing at which failure is found are extracted, and the failure video image 54 is acquired.

It is preferable that the storage mode is set in advance by the user from the contents and the like of the endoscopy. The storage mode is the first storage mode where the sorting processing is not executed and all the failure video images 54 extracted for each failure scene are stored in the main storage region 34, and the second to fourth storage modes where the extracted failure video images 54 are transmitted to and temporarily stored in the temporary storage unit 42 for sorting and the sorting of the failure video images 54 to be stored in the main storage region 34 is performed.

In the first storage mode, the failure video image 54 is extracted from the medical video image 50 temporarily stored in the temporary storage unit 38 based on the initial failure frame image 52 in the failure scene, that is, the reception timing of the trigger signal, and all the extracted failure video images 54 are stored in the main storage region 34.

As shown in FIG. 13, a case where a failure frame image 52*a*, a failure frame image 52*b*, and a failure frame image 52*c* that are different failure scenes are detected from the medical video image 50 in the first storage mode where the sorting is not performed will be described as an example. A failure video image 54*a* having the failure scene of the failure frame image 52*a*, a failure video image 54*b* having the failure scene of the failure frame image 52*b*, and a failure video image 54*c* having the failure scene of the failure frame image 52*c* are extracted and stored in the main storage region 34, based on the trigger signal and the setting of the extraction range. In a case of the first extraction range, each failure video image 54 that is influenced by the length of the failure scene is extracted.

In the second to fourth storage modes, the extraction and the sorting of the failure video images 54 will be described. All the extracted failure video images 54 are temporarily stored in the temporary storage unit 42 for sorting. The failure video images 54 are sorted based on the failure information, and the sorted failure video images 54 are stored in the main storage region 34.

As shown in FIG. 14, a case where a failure frame image 52*a*, a failure frame image 52*b*, and a failure frame image 52*c* that are different failure scenes and have the same type of failure are detected from the medical video image 50 by the failure detection processing in the second to fourth storage modes where the sorting is performed will be described as an example. A failure video image 54*a* having the failure scene of the failure frame image 52*a*, a failure video image 54*b* having the failure scene of the failure frame image 52*b*, and a failure video image 54*c* having the failure scene of the failure frame image 52*c* are extracted and temporarily stored in the temporary storage unit 42 for sorting based on the trigger signal and the setting of the extraction range. After all the failure video images 54 subjected to the sorting processing are temporarily stored, each failure scene is compared by the sorting unit 41, and the sorting is performed following the set sorting criterion. In a case where the failure video image 54*c* is sorted, the failure video images 54*a* and 54*b* are deleted, and the failure video image 54*c* is stored in the main storage region 34.

In the second storage mode and the third storage mode, the sorting of the failure video image 54 for each type of failure is performed. In the failure detection processing, in a case where a plurality of types of failure are detected, at least one failure video image 54 is stored in the main storage region 34. Even in a case where, among a plurality of types of failure, a type of failure that occurs at a high frequency and for which the area of the non-lesion abnormal region T is large and a type of failure that occurs at a low frequency and for which the area of the non-lesion abnormal region T is small are detected in the medical video image 50, in confirming the stored failure video images 54, the failure scene of each type can be confirmed without being overlooked.

In the second storage mode, the failure video image 54 that is stored in the main storage region 34 is sorted based on the type of failure and the time-series order of the reception timing of the trigger signal in the medical video image 50. For example, the failure video images 54 corresponding to N failure scenes from the initial or last failure scene or one failure scene at each given interval among the failure scenes of each failure video image 54 for each type of failure are stored. In the initial failure scene, an elapsed time from the start of the endoscopy is small, and failure other than failure caused by the endoscopy, such as scope dirt, is easily detected. In the last failure scene, in a case where a plurality of types of failure occur, a plurality of types of failure are easily detected in one failure scene. In the sorting at a given interval, conformation can be made whether or not there is failure that occurs in the whole endoscopy.

In the third storage mode, the importance of each failure video image 54 is calculated for each type of failure, and the failure video image 54 that is stored in the main storage region 34 is sorted based on the importance. The importance of each failure scene is calculated and associated with the failure information by the importance calculation unit 43. The importance indicates a possibility of series failure or usefulness for cause analysis of failure. For example, a calculation result of the importance of equal to or greater than 70% or "high" is stored as the failure video image 54, and a calculation result of the importance of less than 70% or "low" is deleted. A calculation method of the importance will be described below. Instead of the evaluation that the importance is equal to or greater than a given value, a given number or a given ratio of failure video images 54 may be sorted in a descending order of the importance from the failure video images 54 temporarily stored in the temporary storage unit 42 for sorting.

In the fourth storage mode, sorting regarding whether or not to individually store the failure video image 54 in the main storage region 34 is performed by user's selection. Specifically, the temporarily stored failure video image 54 are displayed on the display 18 along with the image information including at least the failure information, and the user confirms the reproduced failure video image 54 and the image information, and individually selects the failure video image 54 that is individually stored in the main storage region 34. A user operation in the sorting processing is performed through the user interface 19, and a method of executing a reproduction command or a storage command in a command region 65 with the keyboard, the mouse, the foot pedal, or the like is known. Edition of the image information by a user operation may be performed.

As shown in FIG. 15, instead of a method of reproducing the failure video images 54 in order one by one, the failure video images 54 may be displayed in a list in the image display region 60. It is preferable that the failure video images 54 are displayed in a list in the image display region 60, and the image information of the selected failure video image 54 is displayed in the image information display field 61. Determination regarding whether to store or delete the failure video image may be performed based on the image information. In a case of reproducing the selected failure video image 54, the failure video image 54 may be reproduced as the size displayed in a list or may be temporarily enlarged and reproduced as shown in FIG. 11. It is preferable that the failure static images 55 corresponding to the failure video images 54 that are not being reproduced in the image display region 60 are displayed as thumbnails. A plurality of failure video images 54 may be reproduced at the same time.

The sorting processing is not limited to the contents of the second to fourth storage modes, and sorting conditions of the respective storage modes may be combined. The failure video images 54 may be displayed on the display 18 and conformed after being stored in the main storage region 34.

The sorting processing may be executed at any time each time the failure video image 54 is extracted, instead of after the end of the extraction processing at which all the failure video images 54 are arranged. Sorting is performed by comparing the most recently temporarily stored failure video image 54 and the failure video image 54 newly created by extraction in an either-or format and deleting an unnecessary failure video image. For example, in the third storage mode, the temporarily stored and m-th extracted failure video image 54 and the newly extracted (m+1)th failure video image 54 are compared in importance, and the failure video image having a low importance is deleted. With this, the sorting processing can be performed even in a case where the time or the temporary storage region is restricted.

The function of the sorting unit 41 may be provided inside the processor device 14. In this case, since the trigger signal is transmitted with respect to sorted failure, the medical image processing device 17 may be constantly operated in the first storage mode. The sorting by the processor device 14 may be performed at the same time with the sorting by the sorting unit 41 of the medical image processing device 17. In a case where the sorting is performed at the same time, it is preferable that sorting is performed under different conditions.

A series of flow of the operation to control the extraction and the storage of the failure video images 54 of the present embodiment will be described along a flowchart shown in FIG. 16. The endoscope system 11 acquires the real-time medical video image 50 obtained by imaging the inside of the living body with the endoscope 12 (Step ST110). In the processor device 14 of the endoscope system 11, the failure detection processing of performing detection of the failure frame image 52 from the medical video image 50 and failure determination is executed. The failure static image 55 may be created from the failure frame image 52 (Step ST120). At the same time with the failure detection processing, the medical video image 50 is transmitted to the medical image processing device 17 (Step ST130). In a case where a failure scene is not detected from the medical video image 50 by the failure detection processing (in Step ST140, N), determination is made that there is no failure in the endoscope 12 used in the endoscopy.

In a case where failure is detected in the medical video image 50 by the failure detection processing (in Step ST140, Y), the trigger signal having information regarding the occurrence timing of failure is created (Step ST150). The trigger signal is transmitted to the medical image processing device instantly after the creation (Step ST160). The medical image processing device 17 collates the trigger signal reception timing of the received trigger signal with the medical video image 50 stored in real time, and specifies the trigger signal reception timing (Step ST170). The failure video images 54 having at least the failure scene are extracted from the medical video image 50 following the set extraction range (Step ST180). At the failure detection, in a case where the failure static image 55 is not acquired from the failure frame image 52, the failure static image 55 in which the failure scene of the failure video image is shown is also acquired (Step ST190).

The extracted failure video images 54 may be stored as it is or the failure video images 54 to be stored may be sorted. Determination regarding whether or not to perform the sorting may be performed depending on the storage mode. In a case where the storage mode is the first storage mode, that is, in a case where the sorting of the failure video image 54 is not performed (in Step ST200, N), all the extracted failure video images 54 are stored in the main storage region 34, and the series of flow ends (Step ST230).

In the sorting processing, since the comparison of the failure video images 54 is performed, it is preferable that the sorting processing is executed after the end of the extraction processing, that is, after the endoscopy ends. In a case where the storage mode is the second to fourth storage modes in which the sorting of the failure scenes is performed (in Step ST200, Y), the failure video images 54 are temporarily stored in the temporary storage unit 42 for sorting (Step ST210). Determination regarding whether or not the temporarily stored failure video images 54 satisfy a given criterion or comparison between the failure video images 54 is performed for each storage mode, and the failure video images 54 to be stored are sorted (Step ST220). The sorted failure video images 54 are stored in the main storage region 34, and the series of flow ends (Step ST230).

Second Embodiment

In the above-described first embodiment, a form in which the temporary storage region in temporarily storing the medical video image 50 picked up in real time during the endoscopy and the failure video images 54 is common to any of a volatile memory and a non-volatile memory. In the present embodiment, a form in which temporary storage is performed with respect to a non-volatile memory will be described. The contents common to the above-described embodiment will not be repeated.

The functions of the temporary storage unit 38 and the temporary storage unit 42 for sorting may be realized by a non-volatile memory that maintains stored data even in a state in which no power is supplied to the medical image processing device 17. A situation in which the endoscope system 11 or the medical image processing device 17 is powered off during the endoscopy or a situation in which the medical image processing device 17 is powered off before the failure video images 54 are stored in the main storage region 34 after the end of the endoscopy may occur. Even in such a case, data temporarily stored in the non-volatile memory can be restrained from being lost due to power-off.

In a case of performing sorting, the extracted failure video images 54 are sequentially temporarily stored in the temporary storage unit 42 for sorting that is the non-volatile memory of the medical image processing device 17. In a case where the endoscope system 11 or the medical image processing device 17 is powered off during the endoscopy, determination is made that the endoscopy ends at this point of time, and the sorting of the failure video images 54 starts in a case where power is turned on again. After the end of the endoscopy, the sorting processing is executed, and the sorted failure video images 54 are stored in the main storage region 34.

As shown in FIG. 17, a case where power is turned off during an examination in performing temporary storage with respect to the temporary storage region that is the non-volatile memory will be described. In an examination A, endoscopy ends while power is not turned off, and an examination B is endoscopy in a case where the endoscope system 11 or the medical image processing device 17 is powered off during a real-time examination. In the examination A in which the user operates the end of the endoscopy, the storage of the failure video images 54 is performed as in the first embodiment. In the examination B in which power is turned off and a forced end, not the end operated by the user, occurs, in a case where power is turned on again, the extraction of the failure video images 54 is performed from the medical video image 50 temporarily stored in the non-volatile memory at the point of time at which power is turned off, in a case of the second to fourth storage modes, the sorting is also performed, and the failure video images 54 are stored in the main storage region 34. Temporary storage in the non-volatile memory is performed, whereby imaging can be performed regardless of an end status of the endoscopy, such as a case where power is turned off during the examination, and the extraction of the failure video images 54 from the temporarily stored medical video image 50 and the sorting of the failure video images 54 can be performed.

In regard to storage processing, while the sorted failure video images 54 are transmitted from the non-volatile memory to the main storage region 34 after the sorting processing, there is a case where the medical image processing device 17 is powered off before the end of the sorting or during the storage processing or a case where disconnection occurs in a case where the main storage region 34 is attachable and detachable to and from disconnected from the medical image processing device 17. In a case where the storage processing is interrupted, the failure video images 54 stored in the main storage region 34 and the failure video images 54 that are not stored may not be discriminated. For this reason, an identifier, such as a flag, is set to secure automatic discrimination in extracting the failure video images 54.

In a case of temporarily storing the failure video images 54, different identifiers are set to the respective failure video images 54 after the extraction of the failure video images 54. The identifier is a flag or the like, is preferably set as image information, and is not particularly limited as long as the failure video images 54 can be discriminated. In resuming the interrupted storage processing, the identifier of the failure video image 54 stored in the main storage region 34 is confirmed, and the presence or absence of the failure video image 54 having the same identifier in the temporary storage region as the non-volatile memory is discriminated. The failure video image 54 having the same identifier as the confirmed identifier is not subjected to the storage processing and is deleted from the non-volatile memory.

In a case where the failure video image 54 for which the same identifier is not confirmed is in the temporary storage region, determination is made that the failure video image 54 is not stored in the main storage region 34, and is subjected to the storage processing. The identifier may be used not only in a case where the storage processing is interrupted, but also in confirming whether or not storage is reliably performed even in normal storage processing.

Third Embodiment

In a third embodiment, a form in which, in the failure detection processing, information of the trigger signal is embedded in the medical video image 50, and the failure video images 54 and the failure static images 55 are extracted will be described. The contents common to the above-described embodiment will not be repeated. In the failure specification unit 25 of the processor device 14, a function of a trigger signal application unit (not shown) in a case where the medical video image 50 is edited depending on the creation of the trigger signal is realized.

As shown in FIG. 18, in the processor device 14, the medical video image 50 picked up with the endoscope 12 is edited in real time, and a trigger signal is applied to a frame image in which failure is detected and is transmitted to the medical image processing device 17. It is preferable that the failure detection processing is performed, and the trigger function and the failure information of the trigger signal with respect to the detected failure frame image 52 are embedded in the medical video image 50 as an identifier, such as a failure flag.

The medical image processing device 17 performs the extraction of the failure video images 54 and the failure static images 55 based on the trigger function and the failure information acquired from the processor device of the endoscope system 11 and embedded in the temporarily stored medical video image 50. The extraction is performed from the medical video image 50 with the failure flag applied, whereby it is possible to eliminate an error between the timing at which failure is detected and the frame image to be extracted. It is preferable that the medical video image 50 output from the output control unit 23 is subjected to the failure detection processing. In this case, a frame image being image in the endoscopy is delayed by an amount for the time of the failure detection processing and displayed on the display 15. In a case where the delay of the display causes a problem, the medical video image 50 before the failure detection processing may be transmitted from the output control unit 23 to the display 15.

Fourth Embodiment

In a fourth embodiment, a form in which a second medical video image that is a video obtained by freezing a frame in which failure is detected from the medical video image 50 in the failure detection processing, for a given period is created and is transmitted to the medical image processing device 17 will be described. The contents common to the above-described embodiment will not be repeated. In the failure specification unit 25 of the processor device 14, a function of a second medical video image creation unit (not shown) that creates a second medical video image with the medical video image 50 edited depending on failure detection is realized.

As shown in FIG. 19, in the processor device 14, along with the start of the endoscopy, the medical video image 50 picked up with the endoscope 12 is copied in real time, and the edited second medical video image is transmitted to the medical image processing device 17 along with the medical video image 50. The second medical video image is a video image obtained by recording the same content as the medical video image 50 in a state in which failure is not detected and by recording a video image subjected to freezing for a given time from when failure is detected in a case where failure is detected. Separately from the medical video image 50 and the second medical video image, the trigger signal is also transmitted from the processor device 14 to the medical image processing device 17. The second medical video image that is transferred from the endoscope system 11 to the medical image processing device 17 along with the medical video image 50 is temporarily stored in the temporary storage unit 38.

In the extraction unit 39, at the timing at which the trigger signal from the endoscope system 11 is received, the extraction of the failure video image 54 from the medical video image 50 and the extraction of the failure static image 55 from the second medical video image are performed. The temporary storage of the medical video image 50 and the second medical video image in the temporary storage unit 38 and the timing at which the trigger signal is received are asynchronous, and an error occurs. Along with the reception of the trigger signal, since the same failure frame image 52 continues in a failure scene of the second medical video image, even though the temporary storage and the timing at which the trigger signal is received are asynchronous, the failure static image 55 picked up at the point of time at which failure is detected can be acquired.

It is preferable that failure video image 54 and the failure static image 55 extracted with the same trigger signal are associated with a failure flag or the like and are stored in the main storage region 34. It is preferable that the second medical video image is not stored and is deleted after the extraction of the failure static image 55.

As a modification example of the fourth embodiment, a form in which the failure video image 54 and the failure static image 55 are extracted by a user's operation will be described. A second trigger signal that is a trigger of extraction is created by a freeze operation of the user depressing the freeze button 12*d* in the operating part 12*b* of the endoscope 12 during the endoscopy. The medical image processing device 17 extracts the failure video image 54 from the medical video image 50 and extracts the failure static image 55 from the second medical video image with the reception of the manually created second trigger signal from the endoscope system 11.

The second medical video image in which the video is subjected to freezing for the given period by the freeze operation of the user is transmitted to the medical image processing device 17. The second trigger signal is created in the trigger signal creation unit 27 by the freeze operation and is transmitted to the medical image processing device 17. In a case where the medical image processing device 17 receives the second trigger signal, in the extraction unit 39, the failure video image 54 and the failure static image 55 are extracted from the medical video image 50 and the second medical video image, respectively, and are stored in the main storage region 34.

It is preferable that the failure video image 54 and the failure static image 55 extracted with the trigger signal and the failure video image 54 and the failure static image 55 extracted with the trigger signal are processed such that the user can visually discriminate and are stored. For example, in a case of the extraction with the second trigger signal, it is preferable that the images of the failure video image 54 and the failure static image 55 are processed to be surrounded by a red frame or to have a symbol "Δ" put in an upper right portion thereof. A word "manual" may be added to a file name.

In the above-described embodiment, hardware structures of processing units that execute various kinds of processing, such as the central control unit realized by the processor device 14, the image acquisition unit 21, the input reception unit 22, the output control unit 23, and the failure determination unit 26, the trigger signal creation unit 27, and the static image creation unit 28 included in the failure specification unit 25, the second medical video image creation unit, the central control unit realized by the medical image processing device 17, the data acquisition unit 31, the input reception unit 32, the output control unit 33, and the extraction range setting unit 36, the mode control unit 37, the temporary storage unit 38, the extraction unit 39, the image information management unit 40, the sorting unit 41, the temporary storage unit 42 for sorting, and the importance calculation unit 43 included in the failure video image extraction unit 35 are various processors described below. Various processors include a central processing unit (CPU) that is a general-purpose processor configured to execute software (program) to function as various processing units, a programmable logic device (PLD) that is a processor capable of changing a circuit configuration after manufacture, such as a field programmable gate array (FPGA), a dedicated electric circuit that is a processor having a circuit configuration dedicatedly designed for executing various kinds of processing, and the like.

One processing unit may be configured with one of various processors or may be configured with a combination of two or more processors (for example, a plurality of FPGAs or a combination of a CPU and an FPGA) of the same type or different types. A plurality of processing units may be configured with one processor. As an example where a plurality of processing units are configured of one processor, first, as represented by a computer, such as a client or a server, there is a form in which one processor is configured of a combination of one or more CPUs and software, and the processor functions as a plurality of processing units. Secondly, as represented by system on chip (SoC) or the like, there is a form in which a processor that realizes all functions of a system including a plurality of processing units into one integrated circuit (IC) chip is used. In this way, various processing units may be configured using one or more processors among various processors described above as a hardware structure.

In addition, the hardware structure of various processors is, more specifically, an electric circuit (circuitry), in which circuit elements, such as semiconductor elements, are combined. Furthermore, the hardware structure of the storage unit is a storage device, such as a hard disc drive (HDD) or a solid state drive (SSD).

EXPLANATION OF REFERENCES

10: medical image processing system
11: endoscope system
12: endoscope

12*a*: insertion part
12*b*: operating part
12*c*: distal end part
12*d*: freeze button
13: light source device
14: processor device
15: display
16: user interface
17: medical image processing device
18: display
19: user interface
21: image acquisition unit
22: input reception unit
23: output control unit
25: failure specification unit
26: failure determination unit
27: trigger signal creation unit
28: static image creation unit
31: data acquisition unit
32: input reception unit
33: output control unit
34: main storage region
35: failure video image extraction unit
36: extraction range setting unit
37: mode control unit
38: temporary storage unit
39: extraction unit
40: image information management unit
41: sorting unit
42: temporary storage unit for sorting
43: importance calculation unit
50: medical video image
51: normal frame image
52: failure frame image
52*a*: failure frame image
52*b*: failure frame image
52*c*: failure frame image
53: failure-free abnormal frame image
54: failure video image
54*a*: failure video image
54*b*: failure video image
54*c*: failure video image
55: failure static image
60: image display region
61: image information display field
62: patient ID
63: patient name
64: video image reproduction tool bar
65: command region
C: disconnection
R: lesion region
T: non-lesion abnormal region

What is claimed is:

1. A medical image processing system comprising:

an external device having a processor, the external device being separate from and not included in an endoscope system; and the endoscope system, wherein the processor is configured to:

acquire a real-time medical video image from the endoscope system during endoscopy;

receive a trigger signal from the endoscope system, the trigger signal including information regarding failure occurrence created based on a failure scene of the medical video image, the trigger signal being transmitted via a trigger transmission line separate from a video image transmission line, and being generated in a processor device of the endoscope system by failure detection processing that classifies frame images of the medical video image and specifies the failure scene composed of one or more failure frame images indicating a failure of endoscope equipment;

temporarily store the medical video image in a temporary storage region;

extract a failure video image having the failure scene from the temporarily stored medical video image based on a reception timing of the trigger signal, the failure video image including scenes chronologically before and after the reception timing; and store the failure video image in a main storage region distinct from the temporary storage region, the main storage region comprising non-volatile storage.

2. The medical image processing system according to claim 1, wherein the processor is configured to:

determine a start timing of the extraction based on the reception timing; and extract the failure video image including scenes before and after the reception timing in time series, from the medical video image.

3. The medical image processing system according to claim 1, wherein the processor is configured to:

set a restriction period of the trigger signal after the reception of the trigger signal; and not start the extraction in a case where the trigger signal is received in the restriction period.

4. The medical image processing system according to claim 1, wherein the processor is configured to set an upper limit number for the number of executions of the extraction.

5. The medical image processing system according to claim 1, wherein the processor is configured to:

temporarily store the failure video image; and sort the failure video image to be stored.

6. The medical image processing system according to claim 5, wherein the processor is configured to perform the sorting based on a type of failure and an order of the reception timing.

7. The medical image processing system according to claim 5, wherein the processor is configured to:

calculate an importance of the failure video image based on the information regarding the failure occurrence; and perform the sorting based on the importance.

8. The medical image processing system according to claim 7, wherein the processor is configured to calculate the importance based on visibility of failure or a degree of seriousness of failure.

9. The medical image processing system according to claim 7, wherein the processor is configured to calculate the importance based on a type of an endoscope.

10. The medical image processing system according to claim 5, wherein the processor is configured to perform the sorting of the temporarily stored failure video image and the failure video image newly created by the extraction in an either-or format.

11. The medical image processing system according to claim 1, wherein the processor is configured to perform processing at the extraction such that deletion or browsing of personal information included in image information of the medical video image is disabled.

12. The medical image processing system according to claim 1, wherein the processor is configured to temporarily store the medical video image in a non-volatile memory.

13. The medical image processing system according to claim 12, wherein the processor is configured to sort the failure video image temporarily stored in the non-volatile memory regardless of an end status of the endoscopy.

14. The medical image processing system according to claim 12, wherein the processor is configured to:

set a different identifier to each failure video image at the extraction of the failure video image;

confirm the identifier of the failure video image stored in the main storage region; and delete the failure video image having the same identifier as the confirmed identifier from the non-volatile memory.

15. A method for operating a medical image processing system that includes an external device having a processor, the external device being separate from and not included in an endoscope system, and the endoscope system, the method comprising:

a step of acquiring a real-time medical video image from the endoscope system during endoscopy;

a step of receiving a trigger signal from the endoscope system, the trigger signal including information regarding failure occurrence created based on a failure scene of the medical video image, the trigger signal being transmitted via a trigger transmission line separate from a video image transmission line, and being generated in a processor device of the endoscope system by failure detection processing that classifies frame images of the medical video image and specifies the failure scene composed of one or more failure frame images indicating a failure of endoscope equipment;

a step of temporarily storing the medical video image in a temporary storage region;

a step of extracting a failure video image having the failure scene from the temporarily stored medical video image based on a reception timing of the trigger signal, the failure video image including scenes chronologically before and after the reception timing; and a step of storing the failure video image in a main storage region distinct from the temporary storage region, the main storage region comprising non-volatile storage.

* * * * *